US008808992B2

(12) United States Patent
Gelb et al.

(10) Patent No.: US 8,808,992 B2
(45) Date of Patent: Aug. 19, 2014

(54) SHOC2 MUTATIONS CAUSING NOONAN-LIKE SYNDROME WITH LOOSE ANAGEN HAIR

(75) Inventors: Bruce D. Gelb, Dobbs Ferry, NY (US); Marco Tartaglia, Rome (IT); Len Pennacchio, Berkeley, CA (US); Ravi Iyengar, Mohegan Lake, NY (US); Avi Ma'ayan, New York, NY (US)

(73) Assignees: Icahn School of Medicine at Mount Sinai, New York, NY (US); The Regents of the University of California, Oakland, CA (US)

( * ) Notice: Subject to any disclaimer, the term of this patent is extended or adjusted under 35 U.S.C. 154(b) by 736 days.

(21) Appl. No.: 12/775,396

(22) Filed: May 6, 2010

(65) Prior Publication Data

US 2011/0059851 A1 Mar. 10, 2011

Related U.S. Application Data

(60) Provisional application No. 61/215,568, filed on May 6, 2009.

(51) Int. Cl.
*C12Q 1/68* (2006.01)
*C07K 5/00* (2006.01)

(52) U.S. Cl.
USPC .................. 435/6.12; 530/300; 530/350

(58) Field of Classification Search
USPC ................... 530/300, 350; 435/6.12
See application file for complete search history.

(56) References Cited

U.S. PATENT DOCUMENTS

| | | | |
|---|---|---|---|
| 6,045,996 | A | 4/2000 | Cronin et al. |
| 6,506,889 | B1 | 1/2003 | Han et al. |
| 7,335,469 | B2 | 2/2008 | Gelb et al. |
| 7,928,296 | B2 | 4/2011 | Chicoine et al. |
| 2006/0246470 | A1* | 11/2006 | Fuqua et al. .............. 435/6 |
| 2007/0134655 | A1 | 6/2007 | Bentwich |

FOREIGN PATENT DOCUMENTS

| | | |
|---|---|---|
| WO | WO03029422 | 4/2003 |
| WO | WO2007106407 | 9/2007 |
| WO | WO2008022335 | 2/2008 |
| WO | WO2008061239 | 5/2008 |

OTHER PUBLICATIONS

The nucleic acid sequence search report, AC AEL87058 searched Jan. 14, 2013.*
International Search Report PCT/US/2010/033924 dated Jul. 14, 2010.
Schubbert, S., et al., Hyperactive Ras in developmental disorders and cancer. Nature Reviews Cancer, vol. 7, pp. 295-308 (2007).
Tartaglia, M., et al., Molecular genetics of Noonan syndrome. In: Zenker M. (ed.), Noonan Syndrome and Related Disorders. Monographs in Human Genetics, Basel, Karger, vol. 17, pp. 1-20 (2008).
Tosti, A., et al., Loose anagen hair in a child with Noonan's syndrome. Dermatologica, vol. 182, pp. 247-249 (1991).
Tartaglia, M., et al., Gain-of-function SOS1 mutations cause a distinctive form of Noonan syndrome. Nature Genetics, vol. 39, pp. 75-79 (2007).
Cordeddu, V., et al., Mutation of SHOC2 promotes aberrant protein N-myristoylation and causes Noonan-like syndrome with loose anagen hair. Nature Genetics, vol. 41(9), pp. 1022-1026 (2009).
Mazzanti, L., et al., Noonan-like syndrome with loose anagen hair: a new syndrome? American Journal of Medical Genetics, vol. 118A (3), pp. 279-286, (2003).
EMBL [Online] database accession No. CD743751 (Jun. 29, 2004), IRB1 04_B04_IRB1 04 _030 Infected Rat Blood-fed (IRB) An.gam. 30 hr Abdomen Libary Anopheles gambiae cDNA 5, mRNA sequence.
U.S. Appl. No. 60/662,410, filed Mar. 16, 2005, Johnson et al.
U.S. Appl. No. 60/773,847, filed Feb. 16, 2006, Johnson et al.
U.S. Appl. No. 60/855,308, filed Oct. 31, 2006, Chicoine et al.
U.S. Appl. No. 60/940,567, filed May 29, 2007, Chicoine et al.
Bibliographic data of Chilean Patent No. 200600559, dated Mar. 9, 2007.
Bibliographic data of Chilean Patent No. 200703064, dated May 16, 2008.
Office action issued Sep. 5, 2012, in Chilean Patent Application No. 3369-2008.

* cited by examiner

*Primary Examiner* — Kenneth R. Horlick
*Assistant Examiner* — Joyce Tung
(74) *Attorney, Agent, or Firm* — Fish & Richardson P.C.

(57) ABSTRACT

The present invention is directed to methods of diagnosing Noonan-like syndrome with loose anagen hair comprising detecting a mutation in SHOC2 gene. One specific diagnostic mutation disclosed is an A-to-G transition at position 4 resulting in a mutation at position 2 of SHOC2 amino acid sequence from serine to glycine. The invention also provides related sequences and kits.

21 Claims, 11 Drawing Sheets

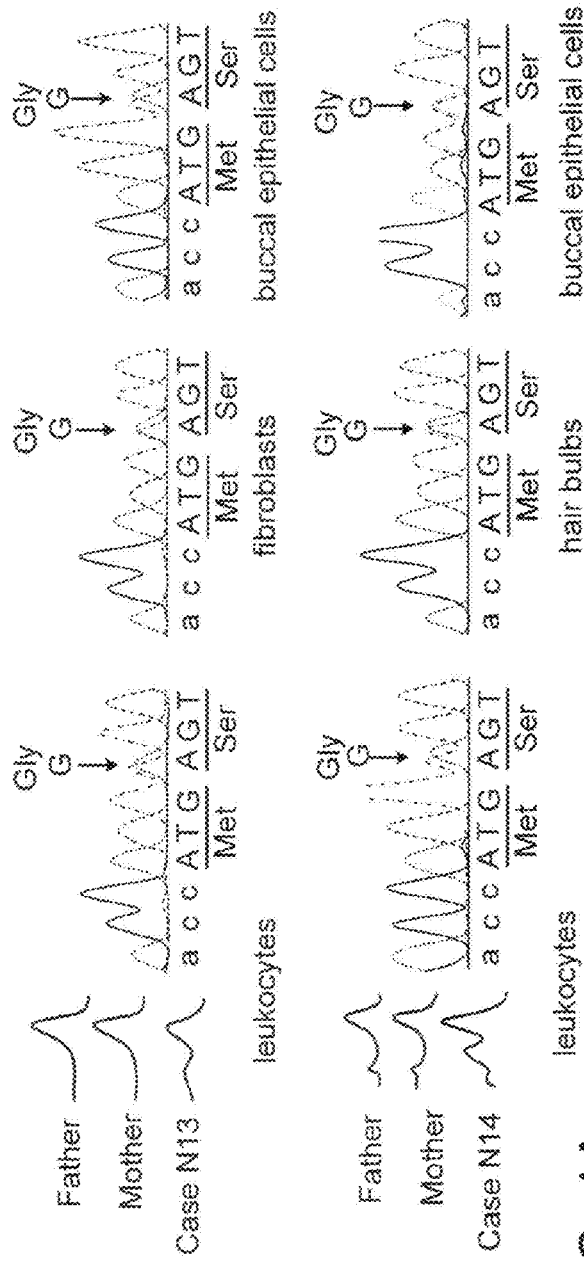
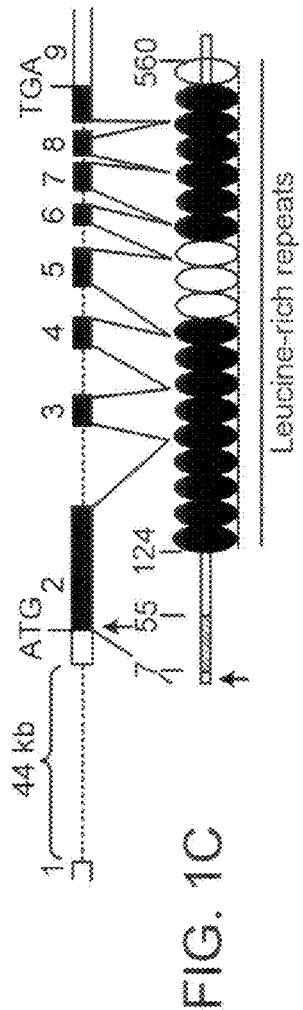
FIG. 1A
FIG. 1C

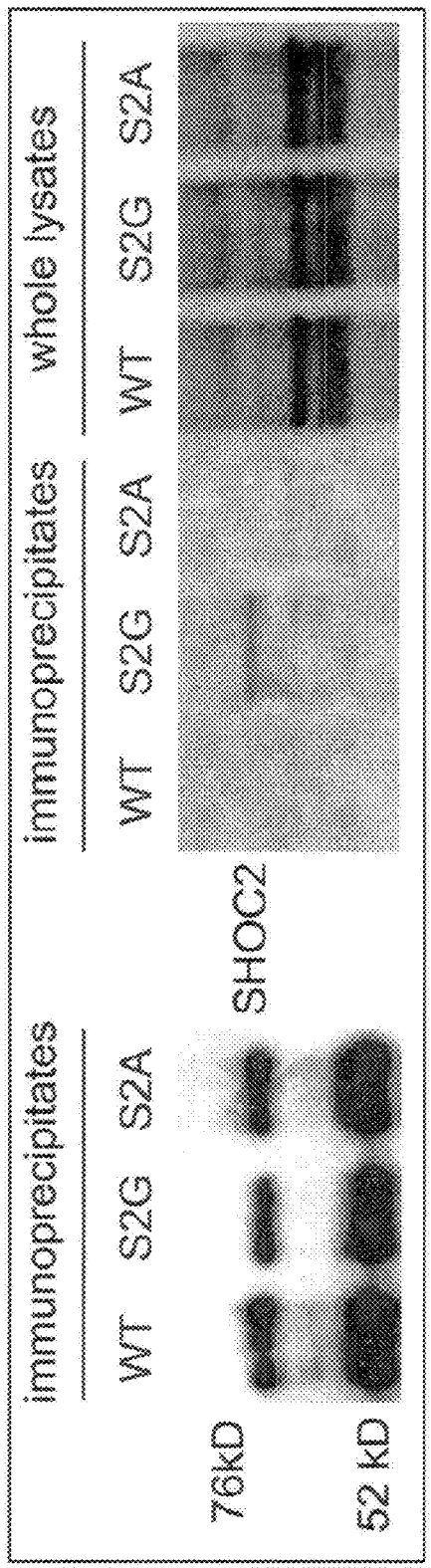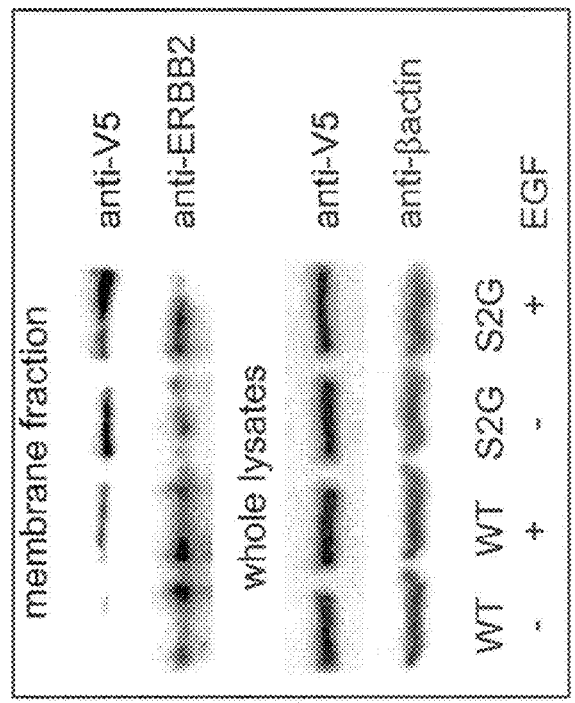

SHOC2 MUTATIONS CAUSING NOONAN-LIKE SYNDROME WITH LOOSE ANAGEN HAIR

This application claims priority from U.S. Provisional Application No. 61/215,568, filed May 6, 2009, which is hereby incorporated by reference in its entirety.

GOVERNMENT SPONSORED RESEARCH OR DEVELOPMENT

This invention was made with government support under grants 5R01HL71207, HD01294 and HL074728 awarded by the National Institutes of Health. The government has certain rights in the invention.

SEQUENCE LISTING

The instant application contains a Sequence Listing which has been submitted via EFS-Web and is hereby incorporated by reference in its entirety. Said ASCII copy, created on Nov. 2, 2010, is named 27527-0064001.txt, and is 18,828 bytes in size.

TECHNICAL FIELD OF THE INVENTION

The present invention is directed to methods of diagnosing Noonan-like syndrome with loose anagen hair comprising detecting a mutation in SHOC2 gene. One specific diagnostic mutation disclosed is an A-to-G transition at position 4 resulting in a mutation at position 2 of SHOC2 amino acid sequence from serine to glycine. The invention also provides related sequences and kits.

BACKGROUND OF THE INVENTION

Dysregulation of the RAS-MAPK signalling pathway has recently been recognized as the molecular cause underlying a group of clinically related developmental disorders with features including reduced postnatal growth, facial dysmorphism, cardiac defects, ectodermal anomalies, variable cognitive deficits and susceptibility to certain malignancies[8,9]. These Mendelian traits, including Noonan, LEOPARD, cardiofaciocutaneous and Costello syndromes, neurofibromatosis type 1 and related phenotypes, are caused by mutations in genes encoding RAS proteins (KRAS and HRAS), downstream transducers (RAF1, BRAF, MEK1 and MEK2), or pathway regulators (PTPN11, SOS1, NF1 and SPRED1). For Noonan syndrome (NS), the most common of these disorders (1:2500 live births), mutations are observed in several of these RAS-MAPK signalling pathway genes, constituting approximately 70% of cases.

Noonan syndrome (NS) is an autosomal dominant, pleiomorphic disorder characterized by short stature, facial dysmorphia, congenital heart defects (e.g., most commonly pulmonic stenosis and hypertrophic cardiomyopathy) and skeletal anomalies (Noonan, Am. J. Dis. Child. 116:373-80, 1968; Allanson, J. Med. Genet. 24:9-13, 1987). Other frequently associated disorders include a webbed neck, chest deformities, cryptorchidism, mental retardation, and bleeding diatheses. NS is a relatively common syndrome with an estimated incidence of 1:1000 to 1:2500 live births. The disorder is genetically heterogeneous and previously identified genes account for approximately only 65% of cases. In addition, there are some closely related disorders, such as Noonan-like syndrome with loose anagen hair, that are difficult to discern, particularly in infants and young children.

Noonan-like syndrome with loose anagen hair refers to disorders described under Online Mendelian Inheritance in Man database of John Hopkins University Accession No. OMIM 607721. Commonly, Noonan-like syndrome with loose anagen hair is characterized by one or more of the following phenotypic features: short stature, certain facial phenotype including high forehead, hypertelorism, palpebral ptosis and low-set and posteriorly rotated ears, macrocephaly, enlarged cerebral spinal fluid spaces, short neck with redundant skin, severe growth hormone (GH) deficiency, mild psychomotor delay with attention deficit/hyperactivity disorder (ADHD), mild dilatation of the pulmonary root, ectodermal abnormalities such as ichthyosis, darkly pigmented and hairless skin, and the unusual aspect of the hair, defined as loose anagen hair syndrome. Reviewed in Mazzanti et al., Am J Med Genet A. 2003, 118A:279-286.

The clinical diagnosis of NS and related disorders such as Noonan-like syndrome with loose anagen hair depends on recognition of the symptoms by a knowledgeable doctor. Nevertheless, substantial phenotypic variations, including mild or subtle cases, make the diagnosis difficult. Furthermore, the facial characteristics become less apparent with progressing age, so the condition will sometimes remain undiagnosed. No genetic test is currently available for diagnosing Noonan-like syndrome with loose anagen hair. Furthermore, currently available genetic tests for diagnosing NS (detecting mutations in PTPN11 and KRAS) account for only 50% of patients suspected of having NS. Therefore, there remains a great need for more specific (e.g., genetic) diagnostics of Noonan-like syndrome with loose anagen hair and other NS-related diseases.

SUMMARY OF THE INVENTION

As specified above, there remains a great need for more specific (e.g., genetic) diagnostics of Noonan-like syndrome with loose anagen hair and other NS-related diseases.

The present invention addresses these and other needs by providing a novel method for diagnosing Noonan-like syndrome with loose anagen hair in a human subject, comprising detecting a mutation in a SHOC2 nucleic acid molecule from the subject, wherein the mutation results in a SHOC2 protein comprising a glycine (Gly) substitution at position 2 of the SHOC2 amino acid sequence, and wherein the presence of said mutation in said SHOC2 nucleic acid molecule is diagnostic of Noonan-like syndrome with loose anagen hair in said human subject.

According to the method of the invention, such diagnostic mutation in a SHOC2 nucleic acid molecule can be detected by any method. In one embodiment, the mutation is detected by a method selected from the group consisting of hybridization (including solution and solid-phase hybridization methods), PCR amplification of a single specified genomic region, microarray-based sequencing, HPLC (including denaturing HPLC (DHPLC)), Denaturing Gradient Gel Electrophoresis (DGGE), Single Strand Conformation Polymorphism (SSCP), HOT cleavage, direct capture-based methods, next generation sequencing, exome sequencing, and whole genome sequencing.

In a preferred embodiment, the diagnostic mutation in a SHOC2 nucleic acid molecule associated with Noonan-like syndrome with loose anagen hair is an A to G transition at position 4 of the SHOC2 coding sequence. In one embodiment, the sequence of the wild-type human SHOC2 nucleic acid is SEQ ID NO: 1, which corresponds to GenBank Accession No. NM_007373, wherein the coding sequence for SHOC2 protein begins at position 350, and the mutant human SHOC2 nucleic acid sequence associated with Noonan-like syndrome with loose anagen hair (SEQ ID NO: 2) has the G substitution at position 4 of the coding sequence of NM_007373 (i.e., position 353). In one embodiment, the wild-type human SHOC2 protein sequence is SEQ ID NO: 3, which corresponds to GenBank Accession No. NP_031399, and the mutant human SHOC2 protein sequence associated with Noonan-like syndrome with loose anagen hair (SEQ ID NO: 4) has the serine (Ser)→glycine (Gly) (Ser2Gly or S2G) substitution at position 2 of NP_031399.

The present invention is also directed to kits for diagnosing Noonan-like syndrome with loose anagen hair, comprising one or more oligonucleotides that specifically hybridize to (or hybridize adjacent to) a site of mutation of a SHOC2 nucleic acid molecule, wherein the mutation results in an amino acid substitution in a SHOC2 polypeptide encoded by the SHOC2 nucleic acid molecule; and instructions for use, wherein the amino acid substitution in the SHOC2 polypeptide is at position 2 of the SHOC2 amino acid sequence. In one embodiment, the amino acid substitution is glycine for serine. In a further embodiment, the site of mutation comprises nucleotide 4 of the SHOC2 coding sequence. In a further embodiment, the mutation at nucleotide 4 of the SHOC2 coding sequence is an A to G transition.

In one specific embodiment, the kit of the invention comprises two oligonucleotides 5'-GTGTAG-GATCTTTGTCTCTTC-3' (SEQ ID NO: 5) and 5'-CCT-TCTTTCCATCTTTGGCAT-3' (SEQ ID NO: 6).

The present invention is also directed to an isolated SHOC2 polypeptide variant comprising a serine (Ser)→glycine (Gly) (Ser2Gly or S2G) substitution at position 2 of the SHOC2 amino acid sequence. In one embodiment, such isolated SHOC2 polypeptide variant has SEQ ID NO: 4. The instant invention is also directed to isolated nucleic acid molecules encoding such a SHOC2 variant. In one embodiment, such nucleic acid molecule has SEQ ID NO: 2.

DETAILED DESCRIPTION OF THE INVENTION

Figure 1B:
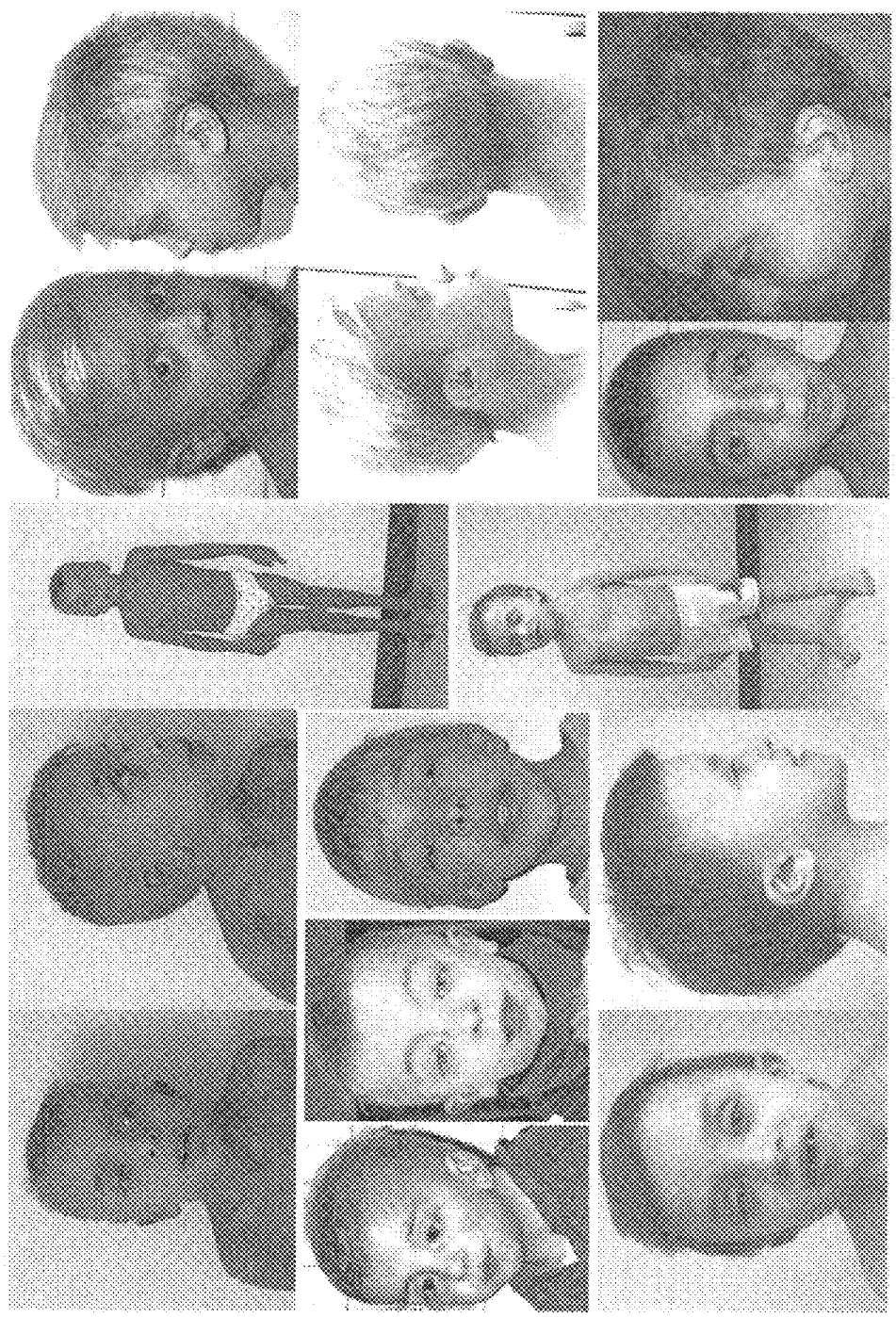
FIG. 1. The germline 4A>G mutation in the SHOC2 gene underlies a distinctive phenotype of the neuro-cardio-facial-cutaneous syndrome family. (a) DHPLC profiles showing the de novo origin of the 4A>G nucleotide change in two affected subjects (left), and electropherograms documenting the heterozygous condition for this mutation at codon 2 in peripheral leukocytes, skin fibroblasts, buccal epithelial cells and/or hair bulb cells from these individuals. (b) Representative phenotypic features of affected subjects carrying the SHOC2 mutation. (c) SHOC2 genomic organization and protein structure. The coding exons are shown at the top as numbered filled boxes. Intronic regions are reported as dotted lines. SHOC2 motifs comprise an N-terminal lysine-rich region (grey coloured; Prosite motif score=8.8, http://www.expasy.ch/tools/scanprosite/) followed by 19 leucine-rich repeats (Pfam hits with an E-value<0.5 are black coloured, while those with an E-value>1 are represented in white, http://pfam.janelia.org/). Numbers above the domain structure indicate the amino acid boundaries of those domains.

The present invention is based on an unexpected discovery that aberrantly acquired N-myristoylation of SHOC2, a cytoplasmic leucine-rich repeat-containing protein that positively modulates RAS-mitogen activated protein kinase (MAPK) signal flow,[3-6] underlies a clinically distinctive condition of the neuro-cardio-facial-cutaneous disorders family. As demonstrated in the Examples section, below, twenty-five subjects with a relatively consistent phenotype termed Noonan-like syndrome with loose anagen hair [OMIM (Online Mendelian Inheritance in Man database of John Hopkins University) 607721][7] shared an A-to-G transition at position 4 in SHOC2 coding sequence that leads to serine (Ser)→glycine (Gly) substitution at position 2 of SHOC2 protein (Ser2Gly or S2G) and introduces an N-myristoylation site, resulting in aberrant targeting of SHOC2 protein to the plasma membrane and impaired translocation to the nucleus upon growth factor stimulation. Expression of mutant SHOC2 protein in vitro enhanced MAPK activation in a cell type-specific fashion. Induction of mutant SHOC2 in *Caenorhabditis elegans* engendered protruding vulva, a neomorphic phenotype previously associated with aberrant signaling. These results provide the first example of an acquired co-translational modification leading to gain of function and causing human disease.

In one embodiment, the sequence of the wild-type human SHOC2 nucleic acid is SEQ ID NO: 1, which corresponds to GenBank Accession No. NM_007373, wherein the coding sequence for SHOC2 protein begins at position 350, and the mutant human SHOC2 nucleic acid sequence associated with Noonan-like syndrome with loose anagen hair (SEQ ID NO: 2) has the G substitution at position 4 of the coding sequence of NM_007373 (i.e., position 353). In one embodiment, the wild-type human SHOC2 protein sequence is SEQ ID NO: 3, which corresponds to GenBank Accession No. NP_031399, and the mutant human SHOC2 protein sequence associated with Noonan-like syndrome with loose anagen hair (SEQ ID NO: 4) has the serine (Ser)→glycine (Gly) (Ser2Gly or S2G) substitution at position 2 of NP_031399.

The subject to whom the diagnostic applications of this disclosure are directed may be any mammal. In a preferred embodiment, the subject is a human. The subject may be of any age (e.g., an adult, a child, an infant), which includes prenatal diagnostics.

In accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

DEFINITIONS

As used herein, the term "Noonan-like syndrome with loose anagen hair" refers to disorders described under Online Mendelian Inheritance in Man database of John Hopkins University Accession No. OMIM 607721. Commonly, Noonan-like syndrome with loose anagen hair is characterized by one or more of the following phenotypic features: short stature, certain facial phenotype including high forehead, hypertelorism, palpebral ptosis and low-set and posteriorly rotated ears, macrocephaly, enlarged cerebral spinal fluid spaces, short neck with redundant skin, severe growth hormone (GH) deficiency, mild psychomotor delay with attention deficit/hyperactivity disorder (ADHD), mild dilatation of the pulmonary root, a unique combination of ectodermal abnormalities including ichthyosis, darkly pigmented and hairless skin, and the unusual aspect of the hair, defined as loose anagen hair syndrome. Reviewed in Mazzanti et al., Am J Med Genet A. 2003, 118A:279-286.

As used herein, the term "Noonan syndrome" or "NS" refers to disorders and diseases described under Accession No. OMIM 163950.

"N-myristoylation" is a common form of protein fatty acylation resulting from the attachment of myristate to a required N-terminal glycine residue.[2]

The term "SHOC2 nucleic acid molecule" refers to a nucleic acid molecule comprising a nucleotide sequence encoding a SHOC2 protein. The terms "SHOC2 coding nucleic acid sequence" or "SHOC2 coding sequence" refer to a portion of a SHOC2 nucleic acid molecule which encodes a SHOC2 protein.

The terms "mutant" and "mutation" mean any detectable change in genetic material or any product, process, mechanism, or result of such a change. When compared to a control material, such change may be also referred to as a "variant" or an "abnormality". This includes gene mutations, in which the structure of a gene is altered, arising from any mutation process, and the structure and/or amount of any expression product (e.g., RNA and/or protein) expressed by such a modified gene is also altered.

As used herein, the term "oligonucleotide" refers to a nucleic acid, generally of at least 10 nucleotides, preferably of at least 15 nucleotides, preferably no more than 100 nucleotides, that is hybridizable to a genomic DNA molecule, a cDNA molecule, or an mRNA molecule. Oligonucleotides can be labeled, e.g., with $^{32}$P-nucleotides or biotin. In one embodiment, an oligonucleotide can be used as a probe to detect the presence of a mutant nucleic acid. A library of oligonucleotides arranged on a solid support, such as a silicon wafer or chip, can be used to detect various mutations of interest. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Diagnostic Methods of the Invention

The present invention is directed to methods for diagnosing Noonan-like syndrome with loose anagen hair in a human subject, comprising detecting a mutation in a SHOC2 nucleic acid molecule from the subject, wherein the mutation results in an SHOC2 polypeptide comprising a glycine substitution at position 2 of the SHOC2 amino acid sequence, and wherein the presence of said mutation in said SHOC2 nucleic acid molecule is diagnostic of Noonan-like syndrome with loose anagen hair in said human subject. In a preferred embodiment, the mutation in the SHOC2 nucleic acid molecule is an A to G transition at position 4 of the SHOC2 nucleic acid sequence.

The above mutation can be detected by any acceptable method. Cost-efficient fast methods suitable for high-throughput use are particularly preferred. Non-limiting examples of such methods include, e.g., solution or solid-phase hybridization methods, PCR amplification of a single specified genomic region, microarray-based sequencing, HPLC (e.g., denaturing HPLC (DHPLC)), Denaturing Gradient Gel Electrophoresis (DGGE), Single Strand Conformation Polymorphism (SSCP), HOT cleavage, direct capture-based methods, next generation sequencing, exome sequencing, and whole genome sequencing.

Denaturing HPLC (DHPLC) can separate heteroduplexes that differ by as little as one base pair. Thus, the use of DHPLC can be applied to point mutation detection (Underhill et al., Genome Research 7:996, 1997; Liu et al., Nucleic Acid Res. 26; 1396, 1998). DHPLC analyses are carried out at a partially denaturing temperature, i.e., a temperature sufficient to denature a heteroduplex at the site of base pair mismatch, homoduplexes can be separated from heteroduplexes having the same base pair length (Hayward-Lester et al., Genome Research 5:494, 1995; Underhill et al., Proc. Nat'l. Acad. Sci. USA 93:193, 1996; Doris et al., DHPLC Workshop, 1997, Stanford University). "Matched Ion Polynucleotide Chromatography" (MIPC), or Denaturing "Matched Ion Polynucleotide Chromatography" (DMIPC) as described in U.S. Pat. No. 6,287,822 or 6,024,878, are separation methods that can also be useful in connection with the present disclosure.

Denaturing Gradient Gel Electrophoresis (DGGE) is a method for resolving two DNA fragments of identical length on the basis of sequence differences as small as a single base pair change, using electrophoresis through a gel containing varying concentrations of denaturant (Guldberg et al., Nuc. Acids Res. 1994, 22:880).

Single Strand Conformation Polymorphism (SSCP) is a method for detecting sequence differences between two DNAs, comprising hybridization of the two species with subsequent mismatch detection by gel electrophoresis (Ravnik-Glavac et al., Hum. Mol. Genet. 3:801, 1994).

"HOT cleavage" is a method for detecting sequence differences between two DNAs, comprising hybridization of the two species with subsequent mismatch detection by chemical cleavage (Cotton, et al., Proc. Natl. Acad. Sci. USA 85:4397, 1988).

The above methods are preferably followed by direct sequencing.

More recently developed techniques using microarrays, preferably microarray techniques allowing for high-throughput screening, can also be advantageously implemented for detecting mutations. Microarrays may be designed so that the same set of identical oligonucleotides is attached to at least two selected discrete regions of the array, so that one can easily compare a normal sample, contacted with one of the selected regions of the array, against a test sample, contacted with another of the selected regions. These arrays avoid the mixture of normal sample and test sample, using microfluidic conduits. Useful microarray techniques include those developed by Nanogen, Inc (San Diego, Calif.) and those developed by Affymetrix. However, all types of microarrays, also called "gene chips" or "DNA chips", may be adapted for the identification of mutations. Such microarrays are well known in the art (see, for example, the following: U.S. Pat. Nos. 6,045,996; 6,040,138; 6,027,880; 6,020,135; 5,968,740; 5,959,098; 5,945,334; 5,885,837; 5,874,219; 5,861,242; 5,843,655; 5,837,832; 5,677,195 and 5,593,839). In principal, any type of array, for example, dot blots on a nylon hybridization membrane (see Sambrook et al., Molecular Cloning A Laboratory Manual (2nd Ed.), Vol. 1-3, Cold Spring Harbor Laboratory, Cold Spring Harbor, N.Y., 1989) could be used, although, as will be recognized by those of skill in the art, very small arrays will be preferred because hybridization volumes will be smaller. For these assays nucleic acid hybridization and wash conditions are chosen so that the attached oligonucleotides "specifically bind" or "specifically hybridize" to at least a portion of a SHOC2 nucleic acid molecule present in a target sample, i.e., the probe hybridizes, duplexes or binds to the SHOC2 locus with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules. It can easily be demonstrated that specific hybridization conditions result in specific hybridization by carrying out a hybridization assay including negative controls (see, e.g., Shalon et al., supra, and Chee et al., Science 274:610-4, 1996).

A variety of methods are available for detection and analysis of a hybridization event. Depending on the reporter group (fluorophore, enzyme, radioisotope, etc.) used to label a probe (e.g., oligonucleotide), detection and analysis are carried out fluorimetrically, calorimetrically or by autoradiography. By observing and measuring emitted radiation, such as fluorescent radiation or a particle emission, information may be obtained about hybridization events. When fluorescently labeled probes are used, the fluorescence emissions at each site of array can, preferably be detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., Genome Res. 6:639-695, 1996).

For description of direct capture-based methods, next generation sequencing, exome sequencing (targeted sequencing of all protein-coding regions), and whole genome sequencing see, e.g., Olson, Nat Methods 2007, 4:891-892; Turner et al., Nat Methods 2009, 6:315-316; Okou et al., Nat Methods 2007, 4:907-909; Albert et al., Nat Methods 2007, 4:903-905; Hodges et al., Nat Genet. 2007, 39:1522-1527; Ng et al., Nat. Genet., 2010, 42:30; Ng et al., Nature, 2009, 461:272; Choi et al., PNAS, 2009, 106:19096; Drmanac et al., Science, 2010, 327:78

The present invention is also directed to kits for diagnosing Noonan-like syndrome with loose anagen hair, comprising an oligonucleotide that specifically hybridizes to (or hybridizes adjacent to) a site of mutation of a SHOC2 nucleic acid molecule, wherein the mutation results in an amino acid substitution in a SHOC2 polypeptide encoded by the SHOC2 nucleic acid molecule; and instructions for use, wherein the amino acid substitution in the SHOC2 polypeptide is at position 2 of the SHOC2 amino acid sequence. In one embodiment, the amino acid substitution is glycine for serine. In a further embodiment, the site of mutation comprises nucleotide 4 of the SHOC2 nucleic acid molecule. In a further embodiment, the mutation at site 4 is an A to G transition.

In one specific embodiment, the kit of the invention comprises two oligonucleotides 5'-GTGTAG-GATCTTTGTCTCTTC-3' (SEQ ID NO: 5) and 5'-CCT-TCTTTCCATCTTTGGCAT-3' (SEQ ID NO: 6).

Example 1

Figure 5:
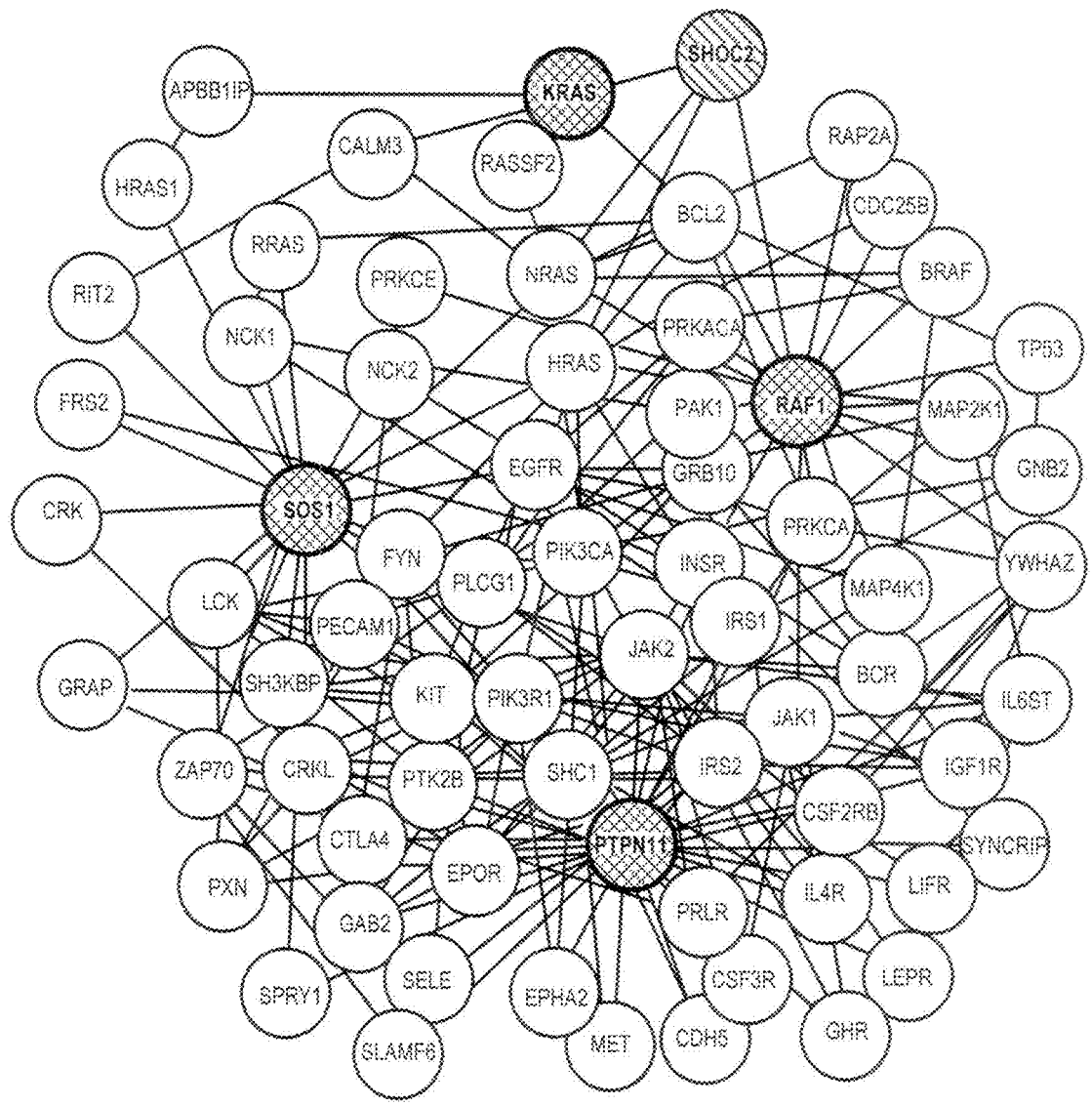
FIG. 5. Mammalian protein-protein interaction network analysis identifies SHOC2 as the best disease gene candidate for Noonan syndrome or a clinically related phenotype. The network was constructed by connecting proteins known to be mutated in Noonan syndrome (cyan) through two nodes/three links using the human interactome. SHOC2, the best candidate, is shown in magenta. Connections indicate protein-protein interactions. Leading candidates and Z scores are reported in Supplementary Table 1.

To rationalize further candidate gene approaches to NS gene discovery, a systems biology approach was used based on in silico protein network analysis. By applying a graph theory algorithm on a filtered consolidated human interactome, a subnetwork of proteins generated from an integrated network of mammalian protein interaction databases and cell-signalling network datasets was derived by seeding with the known RAS/MAPK mutant proteins (FIG. 5).

To identify potential NS disease genes, Z scores were computed using a binomial proportions test, ranking the significance of the intermediate nodes based on their connections to the seed proteins[10] (Table 1).

TABLE 1

Top Noonan syndrome disease candidates predicted by mammalian protein-protein interaction network analysis.

| Protein name | Links for the node | Total links in background | Links to seed | Total links in subnetwork | z-score |
|---|---|---|---|---|---|
| One node/Two links subnetwork | | | | | |
| SHOC2 | 4 | 11184 | 2 | 22 | 22.48034 |
| NRAS | 25 | 11184 | 2 | 22 | 8.80567 |
| CRKL | 34 | 11184 | 2 | 22 | 7.48228 |
| JAK1 | 39 | 11184 | 2 | 22 | 6.95066 |

TABLE 1-continued

Top Noonan syndrome disease candidates predicted by mammalian protein-protein interaction network analysis.

| Protein name | Links for the node | Total links in background | Links to seed | Total links in subnetwork | z-score |
|---|---|---|---|---|---|
| INSR | 41 | 11184 | 2 | 22 | 6.76514 |
| JAK2 | 60 | 11184 | 2 | 22 | 5.48344 |
| BCL2 | 68 | 11184 | 2 | 22 | 5.10772 |
| PRKCA | 91 | 11184 | 2 | 22 | 4.30827 |
| EGFR | 106 | 11184 | 2 | 22 | 3.92713 |
| Two nodes/Three links subnetwork | | | | | |
| SHOC2 | 4 | 11184 | 2 | 223 | 6.86825 |
| RASSF2 | 2 | 11184 | 1 | 223 | 4.85658 |
| SPRY1 | 3 | 11184 | 1 | 223 | 3.88303 |
| FRS2 | 11 | 11184 | 2 | 223 | 3.84067 |
| SLAMF6 | 4 | 11184 | 1 | 223 | 3.29149 |
| APBB1IP | 4 | 11184 | 1 | 223 | 3.29149 |
| GRAP | 5 | 11184 | 1 | 223 | 2.88021 |
| HRAS | 5 | 11184 | 1 | 223 | 2.88021 |
| RIT2 | 7 | 11184 | 1 | 223 | 2.32640 |
| NRAS | 25 | 11184 | 2 | 223 | 2.14823 |
| RRAS | 8 | 11184 | 1 | 223 | 2.12572 |

The top candidates were curated to exclude genes previously screened or those with inappropriate expression patterns. Resequencing of coding exons for the best candidate, SHOC2, in a NS cohort including 96 individuals who were negative for mutations in previously identified disease genes and opportunely selected to represent the wide phenotypic spectrum characterizing this disorder revealed an A-to-G transition at position 4 of the gene, predicting the Ser2Gly amino acid substitution (S2G), in four unrelated individuals (FIG. 1a). This nucleotide change had not been reported in a public SNP database, and $Ser^2$ in SHOC2 is conserved among vertebrate orthologues. All cases were sporadic, and genotyping of parental DNAs available for three of the four subjects documented the absence of the sequence variant in the parents and confirmed paternity in each family, providing evidence that the change was a de novo mutation associated with the disease. For these subjects, DNAs from several tissues were available and all harboured the S2G mutation, providing evidence that the defect was inherited through the germline (FIG. 1a). SHOC2 in a cohort of 410 mutation-negative subjects with NS or a related phenotype was then analyzed. 21 with the 4A>G missense change were observed and proved that mutations were de novo in twelve families from which parental DNAs were available. No additional disease-associated SHOC2 sequence variant was identified in the analyzed cohort, strongly suggesting a specific pathogenetic role for the S2G amino acid substitution.

Review of the features of the SHOC2 mutation-positive individuals revealed a relatively consistent phenotype, previously termed Noonan-like syndrome with loose anagen hair[7] (FIG. 1b). Their features were at first view reminiscent of Noonan syndrome. Phenotype analysis of these subjects, however, was notable for the observation that they exhibited reduced growth associated with proven growth hormone (GH) deficiency, cognitive deficits, distinctive hyperactive behaviour, and hair anomalies including easily pluckable, sparse, thin, slow growing hair. In six subjects, a diagnosis of loose anagen hair (LAH) was confirmed by microscopic examination of pulled hairs, many of which were in the anagen phase but lacked an inner and outer root sheath. Most of them also exhibited hairless and darkly pigmented skin with eczema or ichthyosis. Voice was characteristically hypernasal. Cardiac anomalies were observed in the majority of the cases, with dysplasia of the mitral valve and septal defects significantly overrepresented compared with the general NS population. Overall, these subjects appeared to share a consistent phenotype that was characterized by an unusual combination of features observed in disorders of the neuro-cardio-facial-cutaneous disorders family. Mazzanti et al.[7] reported the new syndrome Noonan-like syndrome with loose anagen hair by detailing three children with short stature, the same facial phenotype, macrocephaly, enlarged spinal fluid space, short neck with redundant skin, severe GH deficiency, mild psychomotor delay with attention deficit/hyperactivity disorder, mild dilation of the pulmonary root in two of them and a unique combination of ectodermal abnormalities.

SHOC2 is a widely expressed protein composed almost entirely by leucine-rich repeats (LRR) and has a lysine-rich sequence at the N-terminus (FIG. 1c). In *C. elegans*, where Shoc2/sur8 was discovered, the protein acts as a positive modulator of the signal transduction elicited by eg1-15 and let-23, and mediated by let-60, homologues of vertebrate FGFR, EGFR and RAS family members, respectively[3,4]. Since LRRs can provide a structural framework for protein-protein interactions, SHOC2 is believed to function as a scaffold linking RAS to downstream signal transducers[4-6]. Based on the N-terminal position of the S2G substitution, the present inventors hypothesized that co-translational processing might be perturbed in the mutant protein, making it a substrate for the N-myristoyltransferase (NMT). N-terminal myristoylation is an irreversible modification occurring co-translationally in which myristate, a 14-carbon saturated fatty acid, is covalently added to an N-terminal glycine residues after excision of the initiator methionine residue by methionylaminopeptidase[1,2]. Glycine at codon 2 is absolutely required, small uncharged residues at positions 3 and 6 are generally needed, and basic residues at positions 8 and 9 are preferred[11]. Save the presence of Ser at position 2, the N-terminal sequence of the SHOC2 satisfied those consensus rules, and in silico analysis predicted myristoylation of the SHOC2$^{S2G}$ mutant with high confidence. To verify this, the myristoylation status of wild type and mutant SHOC2 proteins transiently expressed in Cos-1 cells was evaluated (FIG. 2a). SHOC2$^{S2G}$ incorporated [$^3$H]-myristic acid, while the wild type protein and the disease-unrelated SHOC2$^{S2A}$ did not.

Figure 2B:
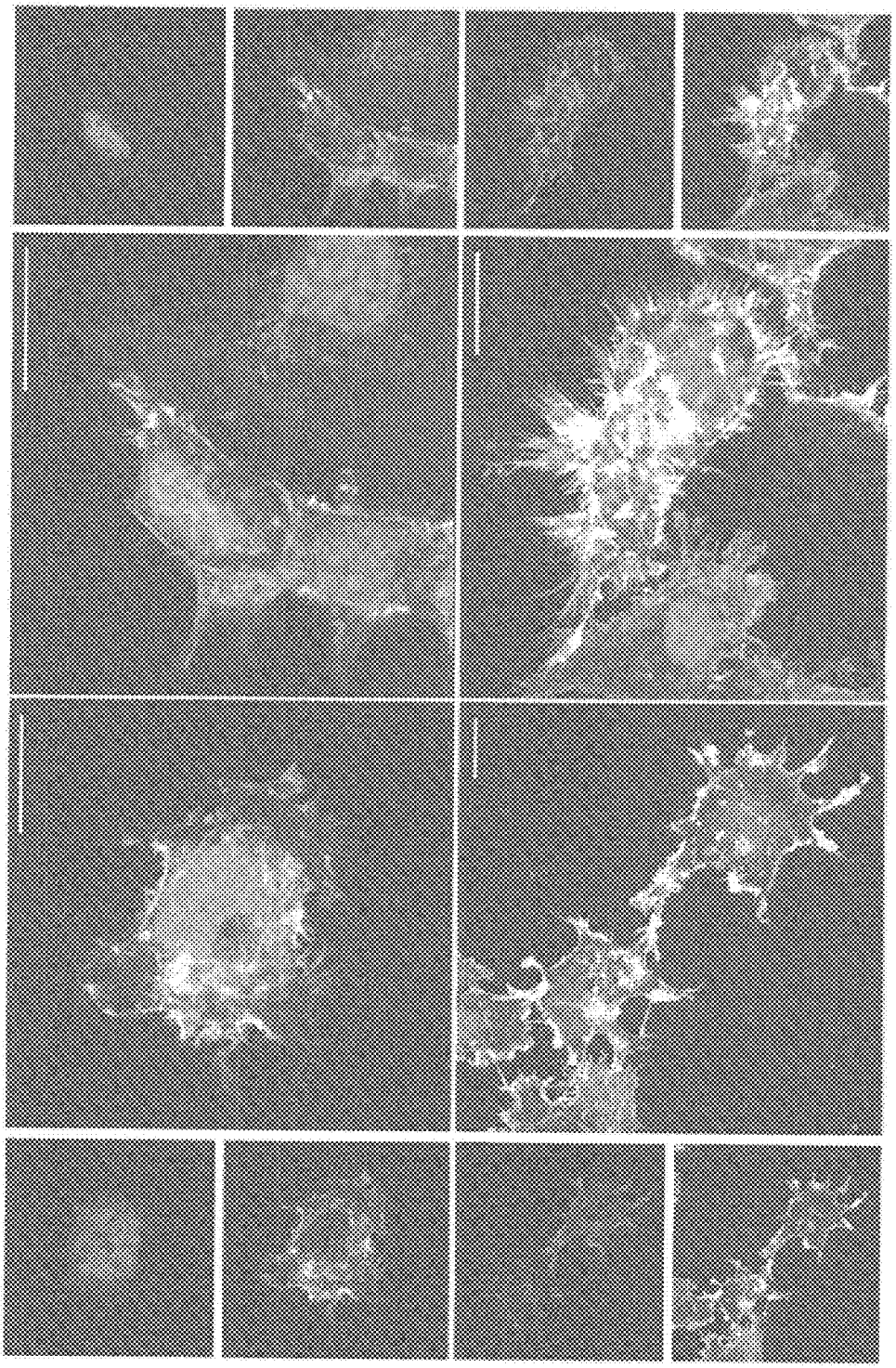
FIG. 2. The disease-causing 4A>G change in SHOC2 promotes protein myristoylation and cell membrane targeting. (a) [$^3$H]myristic acid incorporation (middle) occurs in SHOC2$^{S2G}$ but not in SHOC2$^{wt}$ or SHOC2$^{S2A}$. Equivalent levels of SHOC2 proteins in immunoprecipitates (left) and [$^3$H]myristic acid incorporation in cells (right) are shown. (b) SHOC2$^{wt}$ is uniformly spread in the cytoplasm and nucleus in starved Cos-1 cells (upper left) and is restricted to the nucleus following EGF stimulation (upper right), while SHOC2$^{S2G}$ is targeted to the cell membrane basally (lower left) and after stimulation (lower right). Confocal laser microscopy visualized SHOC2 (anti-V5 monoclonal antibody, then Alexa Fluor-594 goat anti-mouse antibody; red), actin cytoskeleton (Alexa Fluor 488-phalloidin; green) and nuclei (DAPI; blue). Images are single optical sections representative of >50 transfected cells for each experiment. Bars indicate 20 µm. (c) Cell fractioning assay documenting preferential membrane targeting of SHOC2$^{S2G}$. Transiently transfected cells were serum-starved or stimulated with EGF, and lysates were fractionated to separate membrane-associated proteins. ERBB2 is shown to demonstrate equivalent fractionation efficiency, while anti-V5 blot from cell lysates show equivalent transfection efficiency.
Figure 3A:
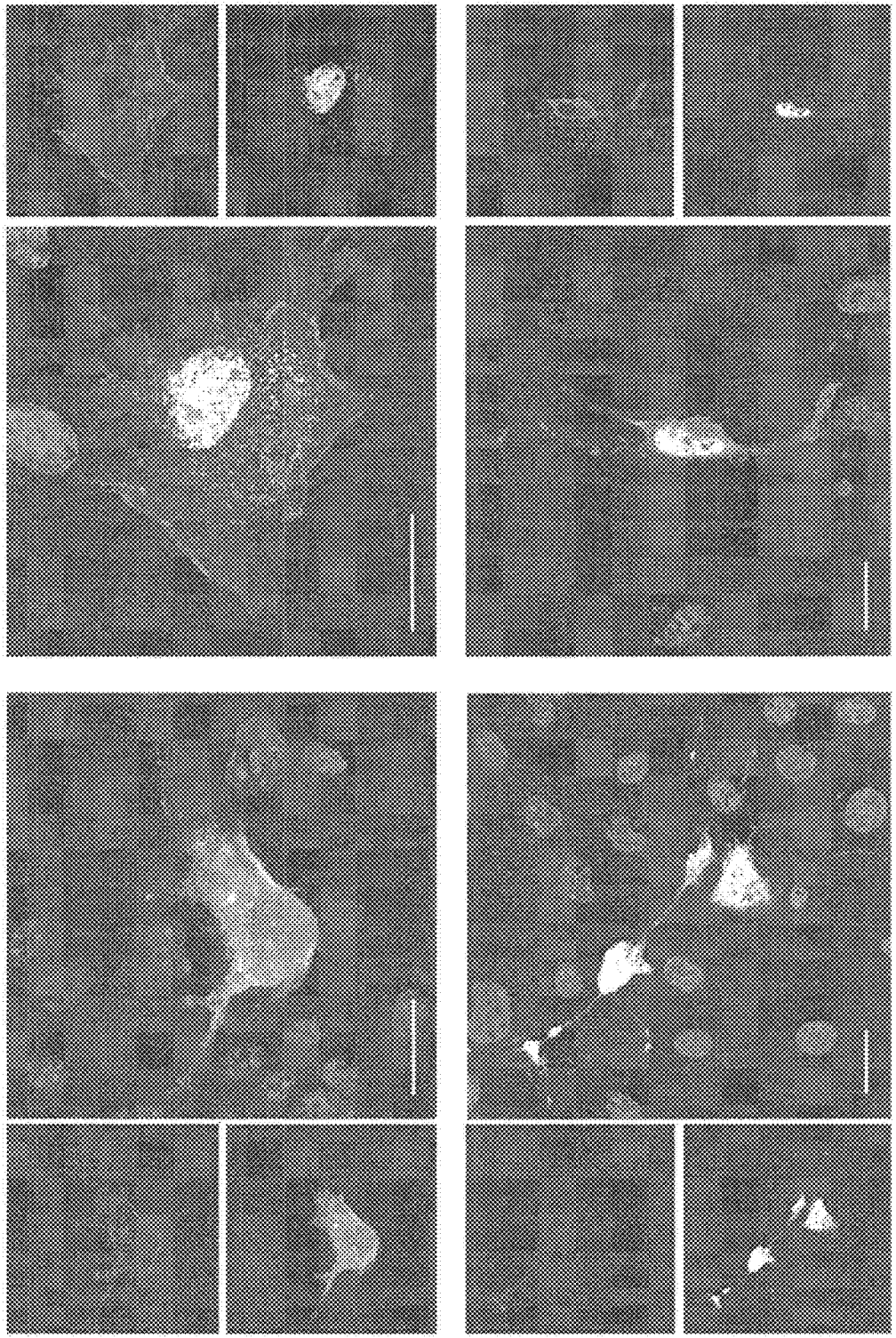
FIG. 3. Functional characterization of the disease-causing 4A>G change in SHOC2. (a) Subcellular localization of co-expressed SHOC2$^{wt}$ (green) and SHOC2$^{S2G}$ (red) documenting that SHOC2$^{S2G}$ does not impair EGF-stimulated SHOC2$^{wt}$ translocation to the nucleus. Imaging of V5-tagged (anti-V5 monoclonal antibody, then Alexa Fluor-594 goat anti-mouse antibody) and Myc-tagged (anti-Myc antibody, then Alex Fluor 488 goat anti-rabbit antibody) SHOC2 proteins and nuclei (DAPI, blue). Panels above show Myc-tagged SHOC2$^{wt}$ and V5-tagged SHOC2$^{S2G}$ and below show V5-tagged SHOC2$^{wt}$ and Myc-tagged SHOC2$^{S2G}$. Cells were imaged basally (left) and following EGF stimulation (right). Bars indicate 20 µm. (b) Lysates of Cos-1 cells co-expressing Myc-tagged SHOC2$^{wt}$ and V5-tagged SHOC2$^{S2G}$ were immunoprecipitated using anti-Myc (above panel) or anti-V5 (below panel) antibody, and immunoprecipitated proteins were visualized by western blotting. These results indicate that SHOC2 proteins do not form heterodimers. (c) ERK phosphorylation in V5-tagged SHOC2$^{wt}$ or SHOC2$^{S2G}$ transiently expressed Neuro2A cells basally or following EGF stimulation.
Figure 3B:
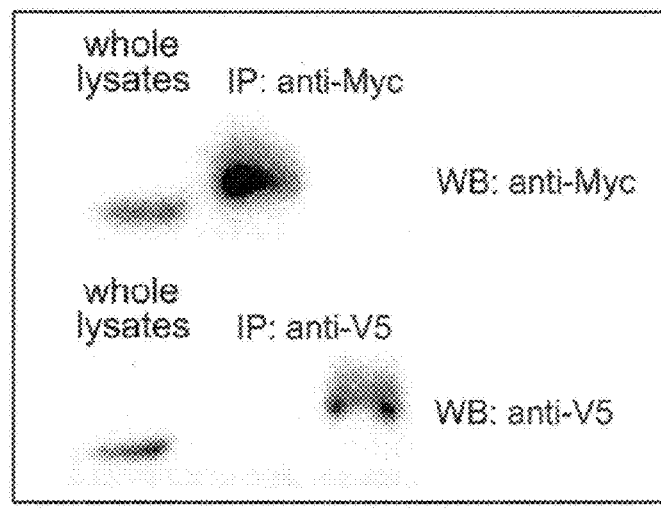
Figure 3C:
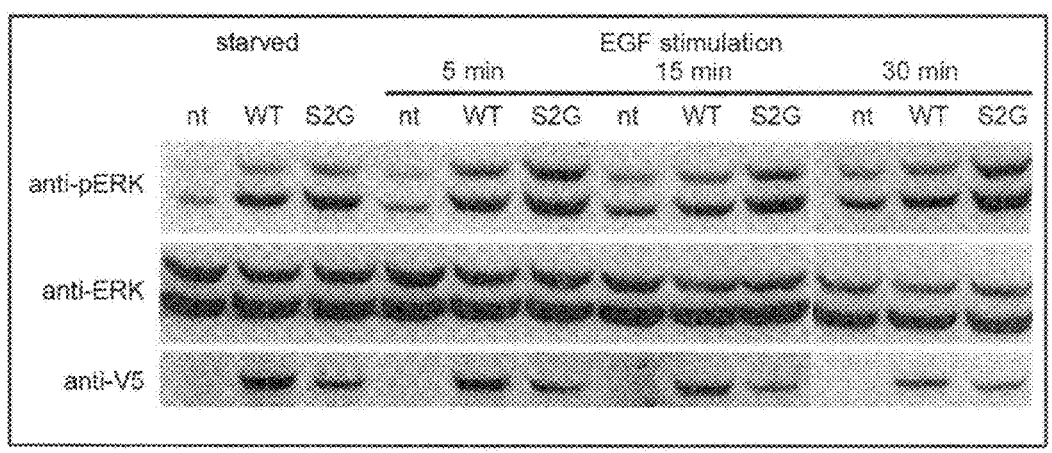
Figure 6:
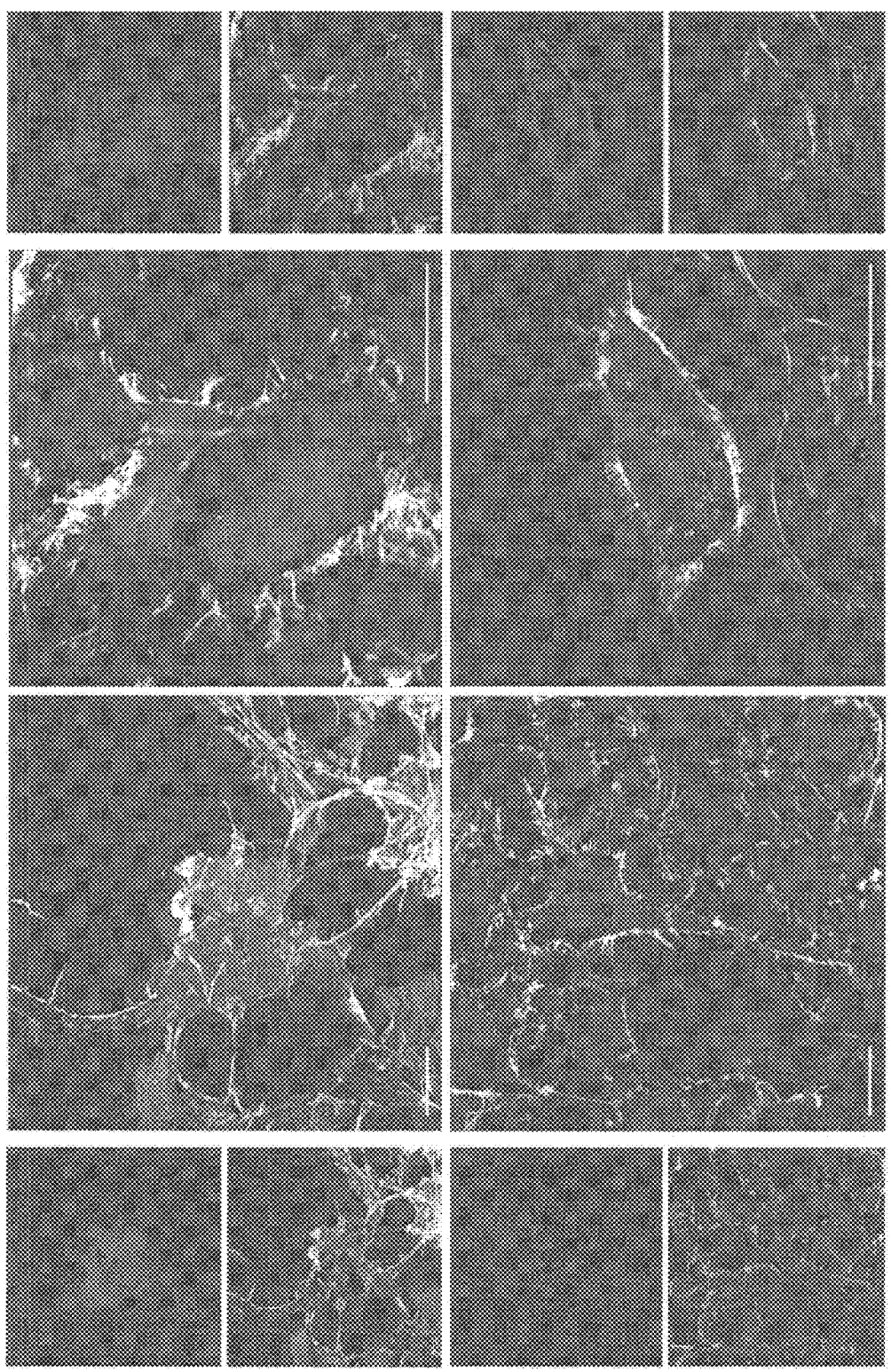
FIG. 6. Subcellular localization of the Myc-tagged SHOC2$^{wt}$ and SHOC2$^{S2G}$ proteins expressed in Cos-1 cells, basally and following EGF stimulation. SHOC2$^{wt}$ is uniformly spread in the cytoplasm and nucleus in starved cells (upper left), and is restricted to the nucleus following stimulation (upper right), while the SHOC2$^{S2G}$ is targeted to the cell membrane in both basal (lower left) and stimulated (lower right) conditions. Confocal laser scanning microscopy was performed using anti-Myc monoclonal antibody, followed by Alexa Fluor-594 goat anti-mouse antibody (red), while actin cytoskeleton was detected by Alexa Fluor 488-phalloidin (green). Nuclei are visualized by DAPI staining (blue). Co-localization areas were detected in yellow. Images represent single optical sections representative of >50 transfected cells observed in each experiment. Bars indicate 20 μm.
Figure 7:
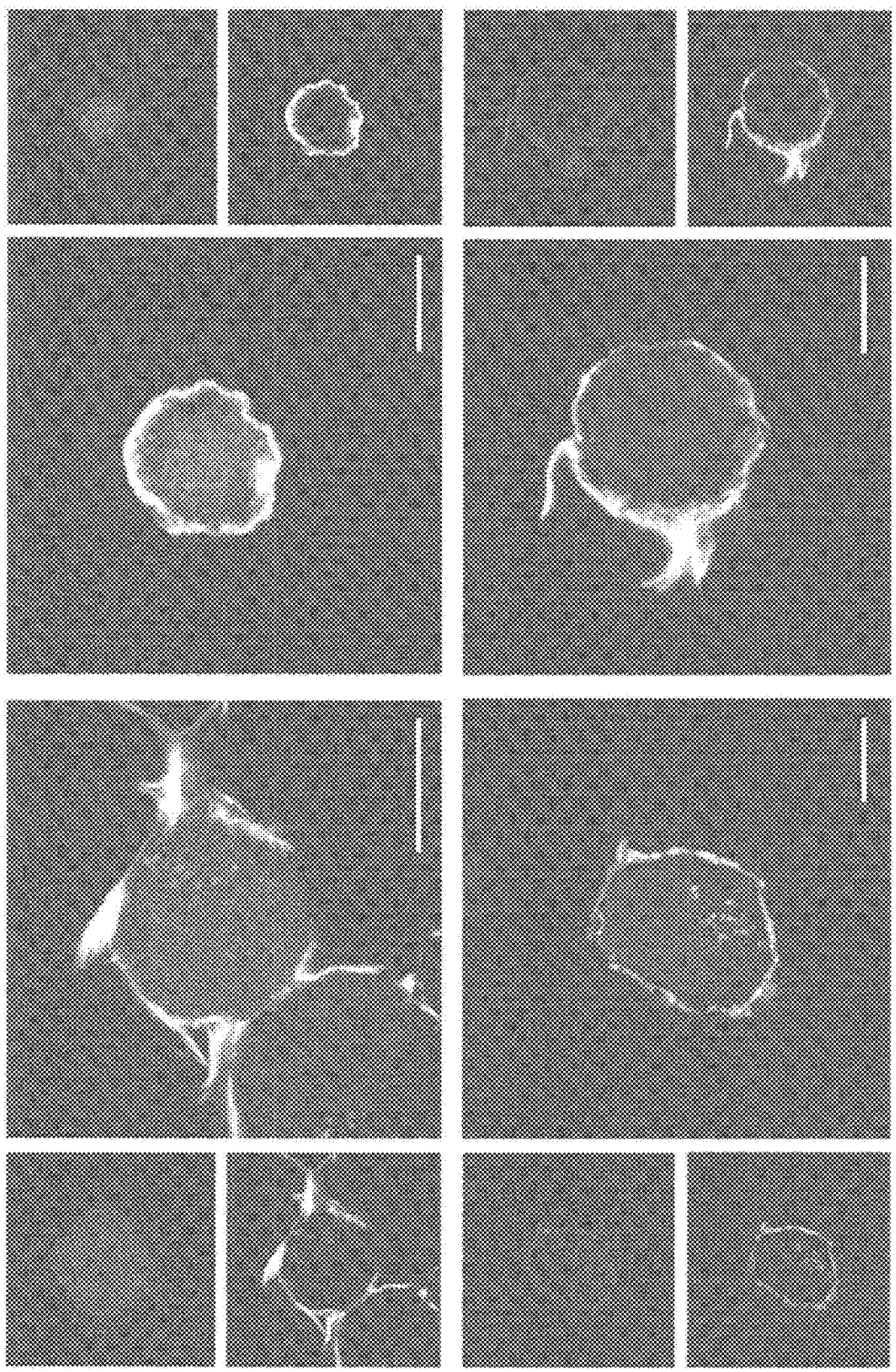
FIG. 7. Subcellular localization of the V5-tagged SHOC2$^{wt}$ and SHOC2$^{S2G}$ proteins expressed in Neuro2A cells, basally and following EGF stimulation. SHOC2$^{wt}$ is uniformly spread in the cytoplasm and nucleus in starved cells (upper left), and is restricted to the nucleus following stimulation (upper right), while the SHOC2$^{S2G}$ is targeted to the cell membrane in both basal (lower left) and stimulated (lower right) conditions. Confocal laser scanning microscopy was performed using anti-V5 monoclonal antibody, followed by Alexa Fluor-594 goat anti-mouse antibody (red), while actin cytoskeleton was detected by Alexa Fluor 488-phalloidin (green). Nuclei are visualized by DAPI staining (blue). Co-localization areas were detected in yellow. Images represent single optical sections representative of >50 transfected cells observed in each experiment. Bars indicate 8 μm.
Figure 8:
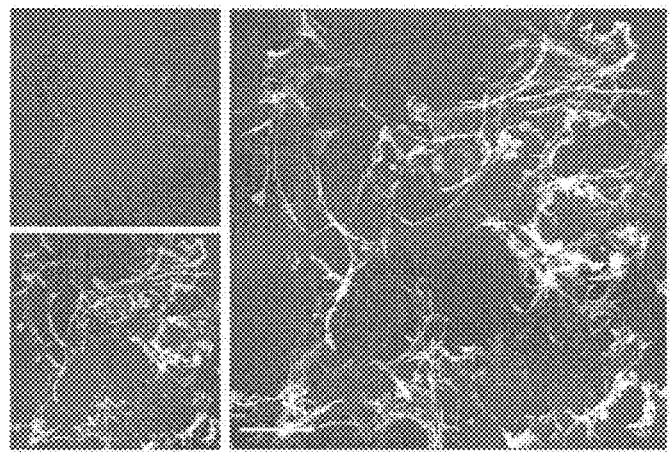
FIG. 8. Myristoylation is required for membrane targeting of the SHOC2$^{S2G}$ mutant. V5-tagged SHOC2$^{S2G}$ is membrane-targeted in untreated Cos-1 cells (top), while membrane targeting is progressively lost in cells treated with an NMT inhibitor (200 μM, middle; 300 μM, bottom). Confocal laser scanning microscopy was performed using anti-V5 monoclonal antibody, followed by Alexa Fluor-594 goat anti-mouse antibody (red), while actin cytoskeleton was detected by Alexa Fluor 488-phalloidin (green). Nuclei are visualized by DAPI staining (blue). Co-localization areas were detected in yellow. Images represent single optical sections representative of >50 transfected cells observed in each experiment. Bars indicate 20 μm.
Figure 8:
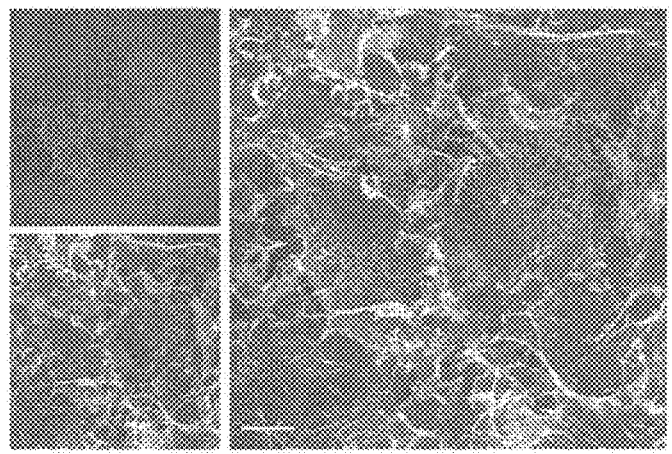
Figure 8:
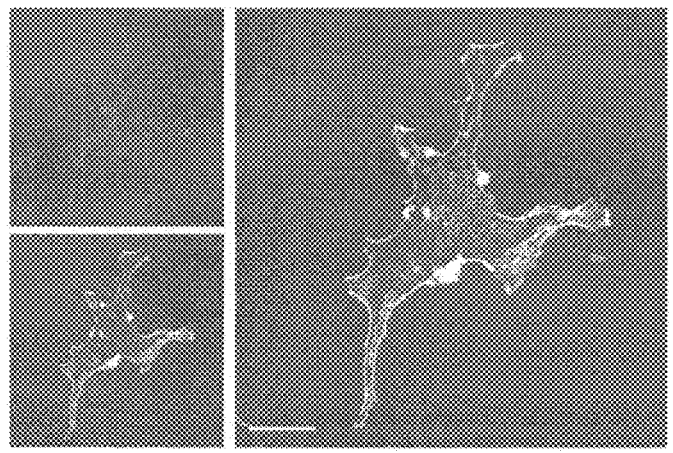

N-myristoylation facilitates anchoring of proteins to intracellular membranes. To explore whether it conferred membrane targeting to mutant SHOC2, the subcellular localization of tagged SHOC2 proteins was analyzed in Cos-1 cells (FIG. 2b and FIG. 6). Confocal laser microscopy analysis documented that SHOC2$^{wt}$ was uniformly distributed in the cytoplasm and nucleus in starved cells but was restricted to the nucleus following EGF stimulation, implying an unexpected role for this protein in signal transduction. In contrast, SHOC2$^{S2G}$ was specifically targeted to the cell membrane in both states. This aberrant localization of SHOC2$^{S2G}$ was confirmed using 293T and Neuro2A cell lines (FIG. 7) and by cell fractionation (FIG. 2c). Treatment with 2-hydroxymyristic acid, an NMT inhibitor, at varying doses reduced or abolished SHOC2$^{S2G}$'s membrane localization (FIG. 8), confirming a dependency upon myristoylation. In addition, even in the absence of efficient myristoylation, the mutant did not translocate to the nucleus upon EGF stimulation, indicating possible loss of function. To exclude the possibility that SHOC2$^{S2G}$ might play a dominant negative effect by sequestering the wild-type protein to the cell membrane, impairing its EGF-dependent translocation to the nucleus, heterodimerization of the wild type and SHOC2$^{S2G}$ proteins was assayed by confocal microscopy and co-immunoprecipitation assays in COS-1 cells transiently co-transfected with V5- and Myc-tagged proteins (FIG. 3a,b). These experiments demonstrated that the wild-type and mutant proteins do not heterodimerize, ruling out that possibility. Next, it was explored whether SHOC2$^{S2G}$ altered intracellular signalling through MAPK. Wild-type and mutant SHOC2 were expressed in Cos-1, 293T and Neuro2A cells. While no significant change in ERK activation in Cos-1 and 293T cells was observed, SHOC2$^{S2G}$ expression promoted enhanced EGF-dependent ERK phosphorylation compared to wild type SHOC2, in neuroblastoma Neuro2A cells (FIG. 3c).

To explore further the functional effects of the SHOC2$^{S2G}$ mutant, *C. elegans* was used as an experimental model. In *C. elegans*, reduced Shoc2/Sur-8 (Sur8$^{rf}$) causes no phenotype but can suppress the gain-of-function Ras (let-60$^{gof}$)-induced multivulva phenotype (Muv)[4]. It was tested whether expression of SHOC2 proteins could rescue the suppressed Muv phenotype in the sur-8$^{rf}$; let-60$^{gof}$ genetic background. While wild type SHOC2 was able to replace Sur-8 functionally, SHOC2$^{S2G}$ failed to do so (STable 2). Expression of the mutant in let-60$^{gof}$ worms did not suppress the Muv phenotype (Table 2), excluding dominant negative effects for SHOC2$^{S2G}$. In a wild-type genetic background, expression of SHOC2$^{S2G}$ at embryonic and early larval stages of development caused no visible phenotype.

TABLE 2

Vulval precursor cell induction in *C. elegans* strains expressing the wild-type or mutant SHOC2 protein.

| | | | | Induction of vulval fate VPC | | | | | | |
|---|---|---|---|---|---|---|---|---|---|---|
| Genotype | Transgene | N | Muv$^a$ | N | P3.p | P4.p | P5.p | P6.p | P7.p | P8.p | Average |
| let-60$^{gof}$ | none | 135 | 68.1 | 39 | 30.8 | 41.0 | 100 | 100 | 100 | 30.8 | 4.0 |
| let-60$^{gof}$; sur-8$^{rf}$ | none | 302 | 7.9 | 85 | 2.4 | 5.9 | 100 | 100 | 100 | 14.1 | 3.2 |
| let-60$^{gof}$; sur-8$^{rf}$ | SHOC2$^{wt}$ | 271 | 19.6$^b$ | 45 | 4.4 | 35.6$^c$ | 100 | 100 | 100 | 37.8 | 3.8$^b$ |
| let-60$^{gof}$; sur-8$^{rf}$ | SHOC2$^{S2G}$ | 104 | 10.6 | 29 | 3.4 | 3.4 | 100 | 100 | 100 | 3.4 | 3.1$^d$ |
| wild type | none | >100 | 0 | | | | | | | | |
| let-60$^{gof}$ | none | 135 | 68.1 | | | | | | | | |

TABLE 2-continued

Vulval precursor cell induction in *C. elegans* strains expressing the wild-type or mutant SHOC2 protein.

| Genotype | Transgene | N | Muv[a] | N | P3.p | P4.p | P5.p | P6.p | P7.p | P8.p | Induction of vulval fate VPC Average |
|---|---|---|---|---|---|---|---|---|---|---|---|
| let-60[gof] | SHOC2[wt] | 72 | 61.1 | | | | | | | | |
| let-60[gof] | SHOC2[S2G] | 132 | 65.9 | | | | | | | | |

Strains: let-60[gof] indicates let-60(n1046), sur-8[rf] indicates sur-8(ku167).
SHOC2[wt] indicates hsp16.2::SHOC2[wt]::V5, SHOC2[S2G] indicates hsp16.2::SHOC2[S2G]::V5.
N indicates the number of animals scored, VPC indicates vulval precursor cell.
Animals were heat-shocked at early L3 stage. Induction of vulval fate is expressed as the percent of individual VPCs (P3.p to P8.p) dividing more than one time. Average refers to the average number of VPCs induced per animal.
P values were calculated using t-Student test for average VPC induction and z statistics for all other proportions.
[a]Muv is expressed as the percent of animals with ectopic pseudovulvae.
[b]Significantly different from the let-60[gof]; sur-8[rf] strain (P < 0.001).
[c]Significantly different from the let-60[gof]; sur-8[rf] strain (P < 0.005).
[d]Significantly different from the let-60[gof]; sur-8[rf] strain expressing the SHOC2[wt] transgene (P < 0.001).

Figure 4:
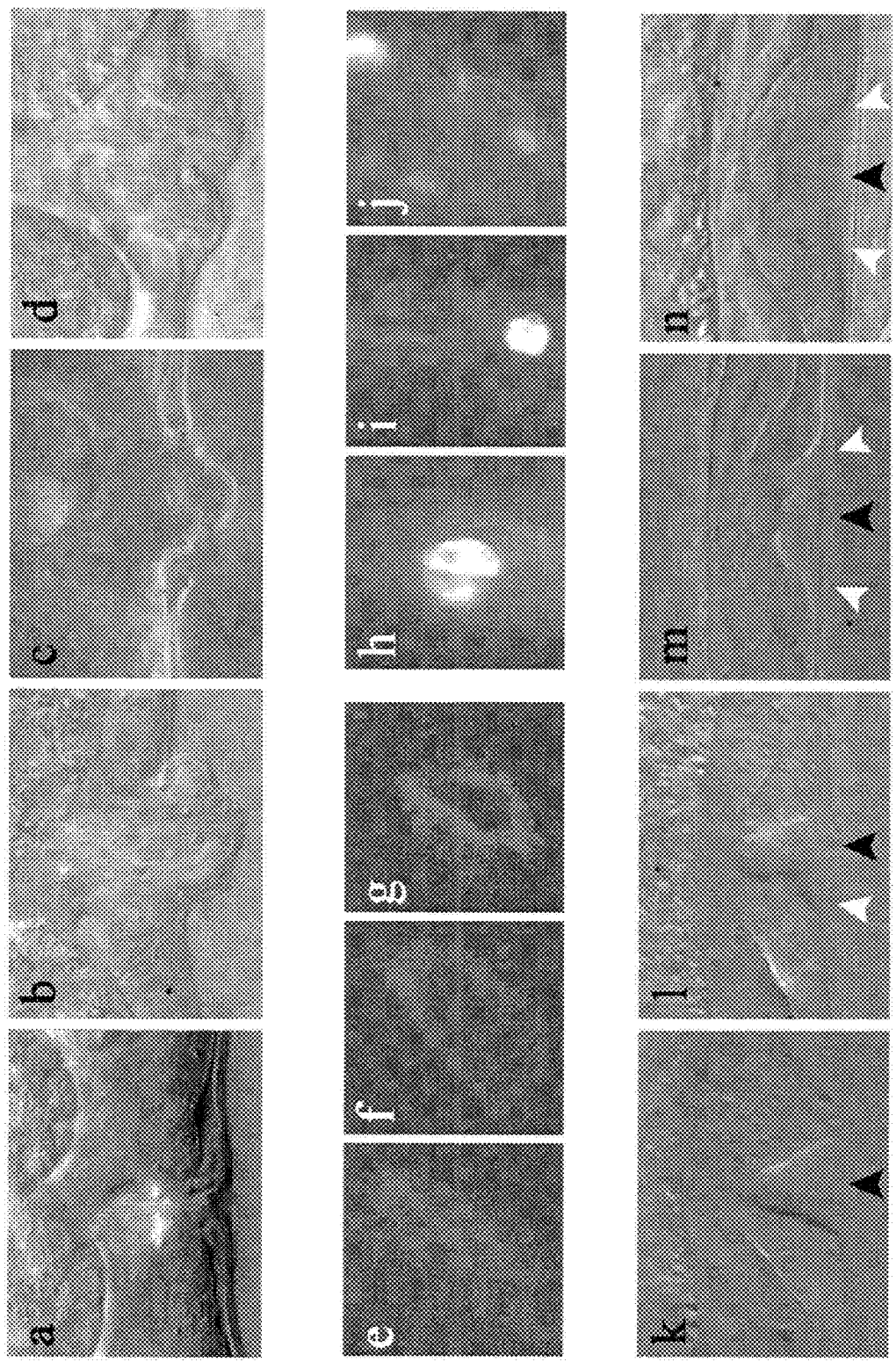
FIG. 4. Consequences of SHOC2$^{S2G}$ expression in C. elegans vulva development. Nomarski images of vulvas of adult animals (a-d). A normal vulva is observed in animals expressing SHOC2$^{wt}$ (a), while in worms expressing SHOC2$^{S2G}$ (b and c) or myr::SHOC2$^{wt}$ (d) a protrusion of the vulva is visible. Subcellular localization of V5-tagged SHOC2 proteins in excretory canal cells (e-g) and intestinal cells (h-j). In both cell types, SHOC2$^{wt}$ protein is present throughout the cytoplasm (e and h), while both SHOC2$^{S2G}$ (f and i) and myr::SHOC2$^{wt}$ (g and j) are enriched in or restricted to the plasma membrane. Confocal analysis was performed by immunofluorescence staining using an Anti-V5 antibody (red). In intestinal cells, nuclei express GFP due to pelt-2::GFP plasmid used as a marker for transformation. Nomarski images of VPCs at L3 stage (k-n). In animals expressing SHOC2$^{wt}$ only P6.p descendant invaginate (k), while in SHOC2$^{S2G}$ (l and m) and myr::SHOC2$^{wt}$ (n) expressing animals also P5.p (l to n) and P7.p descendants (m and n) detach from the cuticle. Anterior is to the left and dorsal is up in all images.

In contrast, its expression at early L3 stage caused abnormal vulval development, resulting in protruding vulva (Pvl), decreased egg laying efficiency (Egl) and accumulation of larvae inside the mother with the formation of bag-of-worms adults (Bag phenotype) (Table 3 and FIG. 4*a-c*). These neomorphic phenotypes were absent in animals expressing SHOC2[wt] but were also observed when SHOC2[wt] tagged with an N-myristoylation sequence (myr::SHOC2[wt]) was expressed (Table 3 and FIG. 4*d*).

TABLE 3

Phenotypes resulting from expression of the SHOC2[wt], SHOC2[S2G] or myr::SHOC[wt] transgene.

| Genotype | Transgene | N | Pvl | N | Egl | N | Bag |
|---|---|---|---|---|---|---|---|
| Wild type | none | 56 | 1.8 | 25 | 19.2 | 20 | 5.0 |
| Wild type | SHOC2[wt] | 44 | 0 | 25 | 16.2 | 20 | 5.0 |
| Wild type | SHOC2[S2G] | 96 | 17.7[a] | 25 | 26.3[a] | 20 | 55.0[d] |
| Wild type | myr::SHOC[wt] | 49 | 36.7[b] | 25 | 25.5[c] | 20 | 45.0[e] |

Animals were heat-shocked at early L3 stage. SHOC2[wt] indicates hsp16.2::SHOC2[wt]::V5, SHOC2[S2G] indicates hsp16.2::SHOC2[S2G]::V5, myr::SHOC2[wt] indicates hsp16.2::myr::SHOC2[wt]::V5.
N indicates the number of animals scored. Pvl is the percent of animals with a protruding vulva.
Egl is the average number of eggs per worm contained in the uterus. Bag is the percent of a bag-of-worms animals 6 days post fertilization.
[a-e]Significantly different from SHOC2[wt] ([a]P < 0.01; [b]P < 0.0001; [c]P < 0.05; [d]P < 0.005; [e]P < 0.02).

The SHOC2[S2G] and myr::SHOC2[wt] proteins were targeted to the cell membrane in various *C. elegans* cell types, while SHOC2[wt] was observed diffusely throughout the cytoplasm and nucleus (FIG. 4*e-j*). The defects in vulva formation were not due to increased induction of the vulva cell fate in vulval precursor cells (VPC) as expression of SHOC2[S2G] did not reduce the vulvaless phenotype of a let-23[rf] hypomorph mutant (Table 4), nor increase the penetrance of the Muv phenotype of let-60[gf] animals (Table 2). At the late L3/early L4 stage, vulva morphogenesis normally begins with the descendants of vulval precursor cell (VPC) P6.p detaching from the cuticle and forming a symmetric invagination. Animals in which the expression of SHOC2[wt] had been induced at early L3 maintained this pattern. In contrast, in larvae expressing SHOC2[S2G] (17/48) or myr::SHOC2[wt] (10/22), descendants of VPCs P5.p and/or P7.p also detached from the cuticle, resulting in larger and asymmetric invaginations (FIG. 4*k-n*). This morphogenesis defect was the earliest detectable neomorphic effect of the SHOC2[S2G] mutation on vulval development and likely underlies the abnormalities seen in the adult vulva.

TABLE 4

Phenotypes observed in *C. elegans* let-23[rf] mutants after expression of the wild-type or mutant SHOC2 transgene.

| Genotype | Transgene | N | Bag |
|---|---|---|---|
| wild type | none | 24 | 0 |
| let-23[rf] | none | 93 | 84.9 |
| let-23[rf] | SHOC2[wt] | 92 | 85.9 |
| let-23[rf] | SHOC2[S2G] | 93 | 95.7[a] | let-23[rf] indicates let-23(sy1), SHOC2[wt] indicates hsp16.2::SHOC2[wt]::V5, SHOC2[S2G] indicates hsp16.2::SHOC2[S2G]::V5.
Worms were heat-shocked at early L3 stage.
N indicates the number of animals scored. Bag is the percent of animals that become a "bag-of-worm" 4 days post-fertilization.
[a]Significantly different from the let-23[rf] strain and the let-23[rf] strain expressing SHOC2[wt] (P < 0.05 in both comparisons).

It is discovered herein that a SHOC2 mutation promoting N-myristoylation of its protein product causes Noonan-like syndrome with loose anagen hair. Acquired co-translational processing, a unique finding for inherited human disease, results in constitutive membrane targeting, leading to increased MAPK activation in a cell context-specific manner. Cell-specific RAS pathway activation has also been observed with NS-associated SHP-2 mutants.[12-14] While not well understood, this phenomenon explains why, despite the ubiquitousness of RAS signalling, development is perturbed in certain tissues in these disorders.

In *C. elegans*, N-myristoylated SHOC2 expression altered morphogenesis during vulval development, a process for which the involvement of Ras signalling is well established. Specification of VPCs was not altered, contrasting with what is noted with many other Ras pathway mutants. Rather, perturbation of the morphogenetic movements of the VPC descendant cells was observed. While numerous mutants altering vulval specification and morphogenesis have been identified, far less is known about processes affecting only morphogenesis.[15,16] It is possible that SHOC2[S2G] alters Ras signalling in steps downstream of the induction of the vulval fate. Alternatively, SHOC2[S2G]-induced vulva defects might arise through perturbation of signalling pathways other than Ras-MAPK, such as signalling mediated by the Rho GTPase, Rac, which is critical for vulval morphogenesis[17].

A unique feature of the SHOC2 mutation is its association with loose anagen hair. This phenotype occurs in isolation or with NS and has been without molecular cause. Hair shafts from affected individuals show features of the anagen stage of hair follicle development, during which epithelial stem cells proliferate in the hair bulb; later stage (telogen) hairs are absent[18]. Hair bulbs lack internal and external root sheaths in this condition. Taken together, these findings suggest perturbation in the proliferation, survival or differentiation of epithelial stem cell-derived cells residing in hair follicles. Our results implicate SHOC2-mediated signal transduction in this aspect of stem cell biology, which must await the availability of a suitable animal model for precise delineation.

Lastly, as disclosed herein, the human interactome and a network-based statistical method were successfully used to predict a novel gene for human disease. The leading candidate, SHOC2, was a relatively obscure gene that caused no phenotype when mutated in worms, evidence of the strength of this approach. For other projects, one can anticipate that successful candidates will not be deemed this favourably, necessitating resequencing of many low-probability candidate genes. Emerging interactome datasets and improved analytic methods are likely to enhance the predictive power of systems biology.

Materials and Methods

Constructing a Mammalian Protein-Protein Interaction Network from Available Resources The protein-protein and signalling networks chosen are all literature-based "legacy" direct biochemical mammalian interactions from low-throughput functional experiments extracted manually by expert biologists (literature-curated). Interactions from high-throughput methods, orthologous interactions from lower organisms, or interactions predicted using in silico methods were not included. Only direct biophysical binding or enzymatic interactions were considered, while interactions based on functional association were excluded. The following available protein-protein interaction datasets were used: DIP[19] (http://dip.doe-mbi.ucla.edu/, May 30, 2006); IntAct[20] (ftp://ftp.ebi.ac.uk/pub/databases/intact/current, Jun. 12, 2006); MINT[21] (http://mint.bio.uniroma2.it/mint-old/release/main.php, May 21, 2006); Ma'ayan et al.[22] (http://www.mssm.edu/labs/iyenear/resources, May 21, 2006); BIND[23] (http://www.bind.ca/, Jan. 24, 2006); PDZ-Base[24] (http://icb.med.cornell.edu/services/pdz/start, Sep. 25, 2006). These datasets were chosen, because components in those networks were annotated with accession codes that permit data consolidation and those datasets were provided freely for analysis and reuse. All interactions from these databases claimed to be direct biochemical interactions determined experimentally, and include the PubMed reference of the research article that describes the experiments used to identify the interactions. Consolidating interactions from the different network databases was accomplished by combining human/mouse/rat gene symbols using the xml version of Swiss Prot (http://www.pir.uniprot.org/database/, on Jun. 21, 2006). The consolidated interactions were stored in a flat file format (http://www.mssm.edu/labs/iyengar/resources/datasets/sig_format.shtml).

Algorithm Used to Generate a List of Novel Ns Candidate Genes.

Problem:

Given a graph G in which a small subset of vertices S, $S \subset G$, are identified as seed nodes in this case known disease genes that cause NS, find a close to minimum connected subgraph G' that includes the seed nodes in S while pruning out intermediate nodes and links that are not statistically significant for interacting with the seed list.

Algorithm:

1. Combine available mammalian protein-protein interaction networks using the method described above.
2. Filter the merged network to prune out interactions from publications reporting high-throughput interaction data as described in Berger et al.[10]
3. Find all shortest paths[31] of length $k_1$ between all pairs of vertices in the merged seed list S'∪S" of all known NS disease genes.
4. Find all edges between intermediate vertices identified in 3. Intermediate vertices, I, are vertices that fall on shortest paths between pairs between all pairs in S'∪S" such that $I \subset G$ and $I \not\subset \{S'\cup S"\}$.
5. Combine all nodes and links found in 3 and 4 to create the subnetwork G'.
6. Rank intermediates base on their links in background network vs. links in subnetwork using a Binomial proportions test as described in Berger et al.[10].

Subjects and Mutation Analysis.

Genomic DNAs from a cohort of 96 subjects with NS or a phenotype suggestive of this disorder without mutation in previously identified disease genes (PTPN11, SOS1, KRAS, HRAS, RAF1, BRAF, MEK1 and MEK2) were screened for the entire SHOC2 coding region using high-throughput resequencing as previously described.[25] All sequence variants identified were verified by manual inspection of the chromatograms and putative causative mutations were verified using another independent sequencing reaction. SHOC2 was then analyzed in a panel of 410 mutation-negative individuals with NS or a clinically related phenotype with denaturing high-performance liquid chromatography and direct sequencing.[25] DNA from skin fibroblasts, hair bulbs and/or epithelial cells from the oral mucosa was extracted using standard protocols. Samples were collected under Institutional Review Board-approved protocols, with informed consent. Permission was obtained to publish the photographs of subjects shown in FIG. 1. When available, parental DNAs were sequenced to establish whether identified changes were de novo. Paternity was confirmed using the AmpF/STR Identifier PCR Amplification Kit (Applied Biosystems).

Functional Analyses.

In silico analysis of protein N-myristoylation was performed using Myristoylator (http://www.expasy.org/tools/myristoylator/), TermiNator (http://www.isv.cnrs-gif.fr/terminator3/index.html) and NMT (http://mendel.imp.ac.at/sat/myristate/index.html) software. The nucleotide substitutions of interest were introduced in V5- and Myc-tagged human SHOC2 cDNA expression constructs by site-directed mutagenesis (QuikChange Site-Directed Mutagenesis Kit, Stratagene). COS-1, 293-T and Neuro2A cells were maintained in DMEM (GIBCO) supplemented with 10% heat-inactivated FCS (Eueoclone) and antibiotics, and transfected at 60-70% confluency, using Fugene6 (Roche) or Lipofectamine 2000 (Invitrogen). N-myristoylation was evaluated by [$^3$H]myristic acid (30 μCi/ml) incorporation as described elsewhere[26]. Proteins immunoprecipitated with an anti-V5 antibody from cell lysates were separated by SDS-PAGE. Gels were fixed, soaked in Amplify™ (Perkin Elmer) for 30 min, dried under a GelAir drying frame (BioRad), and exposed to X-ray film (Kodak) for two months. Cellular fractionation and ERK phosphorylation assays were performed on Cos-1 cells transiently expressing the V5 tagged SHOC2$^{wt}$ or SHOC2$^{S2G}$ using 1 standard protocols[25,27]. Cells were serum starved (16 h) and then stimulated with EGF (30 to 100 ng/ml) for the indicated intervals. In all experiments, a human NMT1 cDNA expression construct (Origene) was co-transfected.

Confocal Laser Scanning Microscopy.

3×10³ cells were seeded on glass coverslips, transiently transfected, serum starved (16 h) and stimulated with EGF (30 ng/ml, 15 min). Cells were fixed with 3% paraformaldehyde (30 min, 4° C.), permeabilized with 0.5% Triton X-100 (10 min, room temperature), and stained as described in the figure legends. Imaging was performed on a Leica TCS SP2 AOBS apparatus, utilizing excitation spectral laser lines at 405, 488 and 594 nm, tuned with an acousto-optical tunable filter. Image acquisition and processing were conducted by using the Leica Confocal Software (Leica Lasertechnik GmbH). Signals from different fluorescent probes were taken in sequential scanning mode.

Generation of *C. elegans* Strains and Phenotypic Analysis.

Culture, maintenance and genetic crosses for nematodes were as described[28]. Nematode strains were provided by the *Caenorhabditis* Genetics Center (University of Minnesota, Minneapolis, Minn.). V5-tagged SHOC2$^{wt}$ and SHOC2$^{S2G}$ cDNA were subcloned into the heat shock inducible pPD49.83 vector (a gift of Andrew Fire, Stanford University School of Medicine, Stanford, Calif.). A chimeric SHOC2 protein, myr::SHOC2$^{wt}$, in which the first seven amino acid residues were substituted by the N-terminal myristoylation signal (MGSCIGK) of src-2 was obtained via PCR amplification and cloned into the pPD49.83 vector. Germline transformation was performed as described[29]. elt-2::GFP (pJM67, a gift from James D. McGhee, University of Calgary, Calgary, Canada), which drives GFP expression in intestinal cells, was used as co-injection marker. At least three independent lines for each construct were tested for the Pvl phenotype after heat shock. All the lines expressing SHOC2$^{S2G}$ or myr::SHOC2$^{wt}$ upon heat shock exhibited a Pvl phenotype. Only the lines carrying the following transgenes were scored quantitatively at the compound microscope and used for further analyses and crosses: gbEx240[hsp16.2::SHOC2$^{WT}$::V5; pelt-2::GFP], gbEx208a[hsp16.2::SHOC2$^{S2G}$::V5; pelt-2::GFP] and gbEx209[hsp16.2::myr::SHOC2$^{wt}$::V5; pelt-2::GFP]. Genetic crosses were performed according to standard methods. For sur-8(ku167), let-60(n1046), gbEx240 and sur-8(ku167), let-60(n1046), gbEx208a double mutants and let-23(sy1); gbEx240 and let-23(sy1); gbEx208a single mutants the presence of sur-8(ku167), let-60(n1046) and let-23(sy1) mutations was confirmed by sequencing the appropriate region of genomic DNA from each transgenic strain. After each cross, isogenic worms that had lost the transgene were cloned separately and used as controls. N2 and derivative strains were maintained and grown at 20° C. unless otherwise specified. The following mutant alleles were used: sur-8$^{rf}$: sur-8(ku167) IV; let-60$^{gof}$: let-60(n1046) IV; let-23$^{rf}$: let-23(sy1) II. Animals were scored blindly at the dissecting microscope to count the number of eggs in utero after cutting the mother (Eg1), animals that had become bags of worms (Bag) and to check for the presence of multiple ectopic pseudovulvae (Muv). A subset of worms was also scored blindly at the compound microscope for vulva morphology and VPC induction phenotypes.

*C. elegans* Heat Shock Experiments, Microscopy and Immunocytochemistry.

At different developmental stages, worms carrying the transgenes were subjected to heat shock at 33° C. for 30 min and then kept at 30° C. for 1 h. Synchronized embryos were heat shocked to study the effects of transgene expression on embryonic and early larval development, while synchronized L1/L2 larvae were heat shocked to study the effects on later larval development, movement and fertility. To study VPC induction and vulva morphogenesis, hermaphrodites were heat shocked at early L3 stages and animals were scored for vulval induction at the L4 stage and for Pvl phenotype at the adult stage. Microscopy observations were performed with a Zeiss Axioskop equipped with epifluorescence and Differential Interference Contrast on live animals anesthetized and mounted on 2% agarose pads containing 10 mM Na-Azide. Images were collected with an Axiocam digital camera. Confocal analyses were performed using a Leica TCS SP2 confocal microscope. For immunocytochemistry analyses, transgenic worms were heat shocked, and after 2 h were fixed with 2% PFA (R.T. 5 min, 1 h on ice). They were processed as reported[30], and then incubated overnight in a dilution of anti-V5 monoclonal antibody (1:200). After repeated washing (24 h), animals were incubated overnight with Texas-Red conjugated anti-mouse secondary antibody (1:100) (Invitrogen), washed and mounted for observation on microscope slides.

The present invention is also described and demonstrated by way of the above examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

All patents, applications, publications, test methods, literature, and other materials cited herein are hereby incorporated by reference in their entirety as if physically present in this specification.

REFERENCES

1. Resh, M. D. Trafficking and signaling by fatty-acylated and prenylated proteins. *Nat Chem Biol* 2, 584-90 (2006).
2. Farazi, T. A., Waksman, G. & Gordon, J. I. The biology and enzymology of protein N-myristoylation. *J Biol Chem* 276, 39501-4 (2001).
3. Selfors, L. M., Schutzman, J. L., Borland, C. Z. & Stern, M. J. soc-2 encodes a leucine-rich repeat protein implicated in fibroblast growth factor receptor signaling. *Proc Natl Acad Sci USA* 95, 6903-8 (1998).
4. Sieburth, D. S., Sun, Q. & Han, M. SUR-8, a conserved Ras-binding protein with leucine-rich repeats, positively regulates Ras-mediated signaling in *C. elegans*. *Cell* 94, 119-30 (1998).
5. Li, W., Han, M & Guan, K. L. The leucine-rich repeat protein SUR-8 enhances MAP kinase activation and forms a complex with Ras and Raf. *Genes Dev* 14, 895-900 (2000).
6. Rodriguez-Viciana, P., Oses-Prieto, J., Burlingame, A., Fried, M. & McCormick, F. A phosphatase holoenzyme comprised of Shoc2/Sur8 and the catalytic subunit of PP1 functions as an M-Ras effector to modulate Raf activity. *Mol Cell* 22, 217-30 (2006).
7. Mazzanti, L. et al. Noonan-like syndrome with loose anagen hair: a new syndrome? *Am J Med Genet A* 118A, 279-86 (2003).
8. Schubbert, S., Shannon, K, & Bollag, G. Hyperactive Ras in developmental disorders and cancer. *Nat Rev Cancer* 7, 295-308 (2007).
9. Tartaglia, M. & Gelb, B. D. Molecular genetics of Noonan syndrome. In *Monographs in Human Genetics. Noonan*

*syndrome and related disorders: A matter of deregulated RAS signalling* (ed. Zenker, M.) 17, 20-39 (Karger Press, Basel, Switzerland, 2009).
10. Berger, S. I., Posner, J. M. & Ma'ayan, A. Genes2Networks: connecting lists of gene symbols using mammalian protein interactions databases. *BMC Bioinformatics* 8, 372 (2007).
11. Boutin, J. A. Myristoylation. *Cell Signal* 9, 15-35 (1997).
12. Tartaglia, M. et al. Somatic mutations in PTPN11 in juvenile myelomonocytic leukemia, myelodysplastic syndromes and acute myeloid leukemia. *Nat Genet.* 34, 148-50 (2003).
13. Araki, T. et al. Mouse model of Noonan syndrome reveals cell type- and gene dosage-dependent effects of Ptpn11 mutation. *Nat Med* 10, 849-57 (2004).
14. Loh, M. L. et al. Mutations in PTPN11 implicate the SHP-2 phosphatase in leukemogenesis. *Blood* 103, 2325-31 (2004).
15. Sternberg, P. W. Vulval development. In *Wormbook* (ed. The *C. elegans* Research Community) WormBook, doi/10.1895/wormbook.1.6.1, http://www.wormbook.org (2005).
16. Eisenmann, D. M. & Kim, S. K. Protruding vulva mutants identify novel loci and Wnt signaling factors that function during *Caenorhabditis elegans* vulva development. *Genetics* 156, 1097-116 (2000).
17. Kishore, R. S. & Sundaram, M. V. ced-10 Rac and mig-2 function redundantly and act with unc-73 trio to control the orientation of vulval cell divisions and migrations in *Caenorhabditis elegans*. *Dev Biol* 241, 339-48 (2002).
18. Tosti, A. et al. Loose anagen hair in a child with Noonan's syndrome. *Dermatologica* 182, 247-9 (1991).
19. Xenarios, I. et al. The Database of Interacting Proteins: 2001 update. *Nucl Acids Res* 29, 239-41 (2001).
20. Kerrien, S. et al. IntAct-open source resource for molecular interaction data. *Nucl Acids Res* 35, D561-D565 (2007).
21. Chatraryamontri, A. et al. MINT: the Molecular INTeraction database. *Nucl Acids Res* 35, D572-4 (2007).
22. Ma'ayan, A. et al. Formation of regulatory patterns during signal propagation in a Mammalian cellular network. *Science* 309, 1078-83 (2005).
23. Bader, G. D., Betel, D. & Hogue, C. W. V. BIND: the Biomolecular Interaction Network Database. *Nucl Acids Res* 31, 248-50 (2003).
24. Beuming, T., Skrabanek, L., Niv, M. Y., Mukherjee, P. & Weinstein, H. PDZBase: a protein-protein interaction database for PDZ-domains. *Bioinformatics* 21, 827-8 (2005).
25. Tartaglia, M. et al. Gain-of-function SOS1 mutations cause a distinctive form of Noonan syndrome. *Nat Genet.* 39, 75-9 (2007).
26. Utsumi, T. et al. Amino acid residue penultimate to the amino-terminal Gly residue strongly affects two cotranslational protein modifications, N-myristoylation and N-acetylation. *J Biol Chem* 276, 10505-13 (2001).
27. Vachon, L., Costa, T. & Hertz, A. GTPase and adenylate cyclase desensitize at different rates in NG108-15 cells. *Mol Pharmacol* 31, 159-68 (1987).
28. Sulston, J. E. & Hodgkin, J. Methods. In *The Nematode Caenorhabditis elegans* (ed. Wood W. B. and the Community of *C. elegans* Researchers) 587-606 (Cold Spring Harbor Laboratory Press, Cold Spring Harbor, N.Y., 1988).
29. Mello, C. C., Kramer, J. M., Stinchcomb, D. & Ambros, V. Efficient gene transfer in *C. elegans* after microinjection of DNA into germline cytoplasm: extrachromosomal maintenance and intergration of transforming sequences. *EMBO J* 10, 3959-70 (1991).
30. Duerr, J. S. Immunohistochemistry. In *WormBook* (ed. The *C. elegans* Research Community,) WormBook, doi/10.1895/wormbook.1.105.1, http://www.wormbook.org (2006).
31. Dijkstra, E. W. A note on two problems in connexion with graphs. *Numerische Mathematik* 1, 269-271 (1959).

What is claimed is:

1. A method for detecting the presence of a SHOC2 mutation associated with Noonan-like syndrome with loose anagen hair in a human subject, comprising:
   (a) determining the sequence of all or a portion of a SHOC2 nucleic acid in a biological sample collected from the subject, wherein the sequence of all or a portion of the SHOC2 nucleic acid is determined by carrying out a method selected from the group consisting of microarray-based sequencing, denaturing HPLC (DHPLC), Denaturing Gradient Gel Electrophoresis (DGGE), Single Strand Conformation Polymorphism (SSCP), HOT cleavage, direct capture-based method, next generation sequencing, exome sequencing, solution or solid-phase hybridization, whole genome sequencing, hybridization, and PCR amplification of a single specified genomic region;
   (b) comparing the SHOC2 nucleic acid sequence in the biological sample from the subject to a nucleic acid sequence encoding a wild-type human SHOC2 protein or comparing the protein sequence encoded by the SHOC2 nucleic acid sequence in the biological sample from the subject to a wild-type human SHOC2 protein sequence; and
   (c) determining that a mutation associated with Noonan-like syndrome with loose anagen hair is present in the subject, when the SHOC2 nucleic acid sequence in the biological sample from the subject encodes a mutant SHOC2 protein comprising glycine (Gly) at position 2 of the SHOC2 protein sequence.

2. The method of claim 1, wherein the mutation associated with Noonan-like syndrome with loose anagen hair is an A to G transition at position 4 of the SHOC2 coding sequence.

3. The method of claim 1, wherein the mutant SHOC2 protein has the sequence SEQ ID NO: 4.

4. The method of claim 1, wherein the mutant SHOC2 nucleic acid molecule has the sequence SEQ ID NO: 2.

5. The method of claim 1, wherein the wild-type human SHOC2 protein has the sequence SEQ ID NO: 3.

6. The method of claim 1, wherein the nucleic acid sequence encoding a wild-type human SHOC2 protein consists of SEQ ID NO: 1.

7. The method of claim 1, wherein step (a) further comprises direct sequencing of said all or a portion of the SHOC2 nucleic acid sequence.

8. The method of claim 1, wherein step (a) comprises carrying out PCR amplification of a single specified genomic region, wherein the PCR amplification comprises:
   (i) contacting DNA obtained from the biological sample collected from the subject or cDNA produced from RNA obtained from the biological sample collected from the subject with a primer pair that allows for specific amplification of all or part of a wild-type and/or mutant SHOC2 genomic DNA or cDNA, under conditions permitting hybridization of the primers to the wild-type and/or mutant SHOC2 genomic DNA or cDNA, wherein the mutant SHOC2 genomic DNA or cDNA encodes a mutant SHOC2 protein comprising glycine (Gly) at position 2 of the SHOC2 protein sequence, and
   (ii) performing the amplification reaction.

9. The method of claim 8, wherein the primer pair consists of 5'-GTGTAGGATCTTTGTCTCTTC-3' (SEQ ID NO: 5) and 5'-CCTTCTTTCCATCTTTGGCAT-3' (SEQ ID NO: 6).

10. The method of claim 1, wherein step (a) comprises carrying out microarray-based sequencing, wherein the microarray-based sequencing comprises contacting DNA or RNA obtained from the biological sample collected from the subject or cDNA produced from RNA obtained from the biological sample collected from the subject with an oligonucleotide that specifically hybridizes to a site of mutation of a SHOC2 nucleic acid molecule, under conditions permitting hybridization of the oligonucleotide to the wild-type or mutant SHOC2 genomic DNA, RNA or cDNA, wherein the mutant SHOC2 genomic DNA, RNA or cDNA encodes a mutant SHOC2 protein comprising glycine (Gly) at position 2 of the SHOC2 protein sequence.

11. The method of claim 1, comprising, prior to step (a), producing cDNA from RNA contained in the biological sample from the subject.

12. The method of claim 1, comprising, prior to step (a), collecting the biological sample comprising DNA or RNA from the subject.

13. A method for diagnosing a subject as afflicted with or predisposed to Noonan-like syndrome with loose anagen hair, said method comprising:
   (a) determining the sequence of all or a portion of a SHOC2 nucleic acid in a biological sample collected from the subject, wherein the sequence of all or a portion of the SHOC2 nucleic acid is determined by carrying out a method selected from the group consisting of microarray-based sequencing, DHPLC, DGGE, SSCP, HOT cleavage, direct capture-based method, next generation sequencing, exome sequencing, solution or solid-phase hybridization, whole genome sequencing, hybridization, and PCR amplification of a single specified genomic region;
   (b) comparing the SHOC2 nucleic acid sequence in the biological sample from the subject to a nucleic acid sequence encoding a wild-type human SHOC2 protein or comparing the protein sequence encoded by the SHOC2 nucleic acid sequence in the biological sample from the subject to a wild-type human SHOC2 protein sequence; and
   (c) diagnosing the subject as being afflicted with or predisposed to Noonan-like syndrome with loose anagen hair, when the SHOC2 nucleic acid sequence in the biological sample from the subject encodes a mutant SHOC2 protein comprising glycine (Gly) at position 2 of the SHOC2 protein sequence.

14. The method of claim 13, wherein the mutation associated with Noonan-like syndrome with loose anagen hair is an A to G transition at position 4 of the SHOC2 coding sequence.

15. The method of claim 13, wherein the mutant SHOC2 protein has the sequence SEQ ID NO: 4.

16. The method of claim 13, wherein the mutant SHOC2 nucleic acid molecule has the sequence SEQ ID NO: 2.

17. The method of claim 13, wherein the wild-type human SHOC2 protein has the sequence SEQ ID NO: 3.

18. The method of claim 13, wherein the nucleic acid sequence encoding a wild-type human SHOC2 protein consists of SEQ ID NO: 1.

19. The method of claim 13, comprising, prior to step (a), producing cDNA from RNA contained in the biological sample from the subject.

20. The method of claim 13, comprising, prior to step (a), collecting the biological sample comprising DNA or RNA from the subject.

21. A method for detecting the presence of a SHOC2 mutation associated with Noonan-like syndrome with loose anagen hair in a human subject, the method comprising:

(a) obtaining nucleic acid from a biological sample collected from the subject;

(b) analyzing, using an automatic computerized sequencer, the nucleic acid to determine its nucleotide sequence;

(c) comparing, with software programmed to perform a base-by-base comparison, the nucleotide sequence of the nucleic acid to a nucleotide sequence encoding a wild-type human SHOC2 protein;

(d) providing for display on a computer, the difference between the nucleotide sequence of the nucleic acid and the nucleotide sequence of the wild-type human SHOC2 protein; and (e) determining that a mutation associated with Noonan-like syndrome with loose anagen hair is present in the subject when the nucleic acid comprises a nucleotide sequence that encodes a mutant SHOC2 protein comprising glycine (Gly) at position 2 of the SHOC2 protein sequence.

* * * * *

SEQUENCE LISTING

```
<160> NUMBER OF SEQ ID NOS: 6

<210> SEQ ID NO 1
<211> LENGTH: 3962
<212> TYPE: DNA
<213> ORGANISM: Homo sapiens

<400> SEQUENCE: 1 gagtgggga ggggcggcg gggggcggcg gttgggcagc gtcgcttctt aggaggagga      60
ggaagaggag gaaggagggc gagcgaggag gatggcggag tcggggctcc tgacggaact     120
ctaatgaatc attgattgac cagcactatt ttaccagttg gaatgaatga tcagaaatgg    180
gcatagtgct tttagatcca acatgtaaca gatggatgtt actccatgct gattacttct    240
tcaagccagt acttttttga ttgtgtagga tctttgtctc ttcatctttg aattcaatta    300
ctggaaaata aaaggagttc atgtagtttt tgtccaggct tgagtcacca tgagtagtag    360
tttaggaaaa gaaaaagact ctaaagaaaa agatcccaaa gtaccatcag ccaaggaaag    420
agaaaaggag gcaaaagcct ctggaggttt tgggaaagag agcaaagaaa aagaacctaa    480
gaccaaaggg aaagatgcca aagatggaaa gaaggactcc agtgctgccc aaccagggt     540 ggcattttca gttgacaata cgatcaaacg gccaaaccca gcacctggga ctagaaaaaa    600
atccagcaat gcagaggtga ttaaagagct caacaaatgc cggaagagaa attcaatgcg    660
tttggactta tccaagagat ctatacacat attgccatca tcaatcaaag agttgactca    720
```

```
attaacagaa ctttatttat acagtaacaa attgcagtcc ctcccagcag aggtgggatg      780
tttagtaaat ctcatgacac tggctctaag tgaaaattca cttaccagtt tgcctgactc      840
tcttgataac ttgaagaagc tgcggatgct tgatttacgg cataataaac tgagagaaat      900
tccttcagtg gtgtataggc tggattctct caccactctt taccttcgct ttaatcgtat      960
aactactgtg gaaaaggaca tcaaaaactt gtcaaaactc agcatgctta gcattcgaga     1020
gaacaaaatt aaacaactac ctgctgaaat tggtgaatta tgtaacctca ttacgctgga     1080
tgtagctcac aatcaacttg aacaccttcc aaaggagatt ggaaactgta cacagataac     1140
caaccttgac ttgcagcaca atgaactgct agacctccca gatactatag aaacctgtc      1200 cagtttaagt cgtcttggtc tgagatataa cagactgtca gcaatacccca gatcattagc     1260 aaaatgcagt gcacttgaag aattaaattt agagaacaat aacatttcta ctttaccaga     1320
gagtctttta tcaagtcttg tgaaactgaa tagtttgacc ttagctagaa attgcttcca     1380
gttgtatcca gtgggtggtc catctcagtt ttctaccatc tattccctca acatggaaca     1440
caatcgaatc aacaaaattc catttggaat tttctccaga gcaaaagtat taagtaagct     1500
gaatatgaag gacaatcagt taacatcact tcccttggat tttggaactt ggaccagtat     1560
ggtagaattg aatttagcca ctaatcagct cacaaagatc cctgaggatg tgtctggtct     1620 cgttctctt gaggttctta tcttatcaaa caatcttcta aagaagcttc cccatggtct     1680
tggaaacctt aggaagttaa gagagttgga tctagaagag aacaaattgg aatccttgcc     1740
aaatgaaatt gcatatctta aggatttaca gaaattagtc ttgacaaaca accagttgac     1800
cactcttccc agaggcattg gtcaccttac taatctcaca catctgggcc ttggagagaa     1860
cctacttact caccttcctg aagaaattgg tacactggag aacctagaag aactgtatt      1920 gaatgacaac cccaacctgc atagccttcc ctttgagctg gcactctgca gcaagctttc     1980
aatcatgagt attgagaact gtccactcag tcaccttcca cctcagattg ttgctggggg     2040
gccttctttc atcattcagt tcttaaagat gcagggtcca tatcgtgcca tggtctgata     2100
taaatctgct ggtcccacac actgttcaaa aatagactgc cattaatgtt tcttatctat     2160
atctgtatct atttatgtag atattggtat atggcagatt tataaaaatt gcattatgtg     2220
tttctgctaa tagaggaatc atagccattt agaattttt ttaaattctg tacaaaaggc     2280
ttatataagt tttcttgct gaatttgatg atgttttc tgttgtgtaa tctgatatgc      2340
cagtttgctt aaaacatttg ccaacacatt atgaagttat taaatttaag ggacagaggt     2400
agtatagtta gatatacttt ctcttaggaa aaataatggg caaaaatttt tgttgcaact     2460
tttcatatat attttcccct taccaattgt tttatcctta tagtattgta ggccctgaaa     2520 gtagaattt tctttaactt attttgagat ttgagattta aatttatgt attgtttaca      2580 gtcagagtaa atcactggat ttcttttgtt tgttttgatt tgctctgttt tattcagtca     2640
aatctagagt ttgaatcctc tgctaaagaa tttgcatcca ctggtgtaaa cagtgaaagg     2700
tatttgcttg ttgaaaaaaa aaactggcaa agtgaaaaga tacagtcaaa aatctagaat     2760
ttctttaatt ttgcttctct gacgagttgt gaagcaaaat acctgaagtg agtctttggg     2820
taggggaagg gtattgagac cttttctagt atgaatattt tttaagtttg ggggaagaga     2880
aacttgcagt gaaaaggagt ttttcattc ctgaaagttg cagatccaca aaactaacag      2940
gataattggg caaataaatt acatataaac acacacaatc tatatatgta tatacaatgc     3000
tatatagata tgtatttatt atatcataaa ctacagtagg taactttaag gatttcttcc     3060
```

-continued

```
tatccttgta caatgacatg aatgtctttc tttgaaaact gcaatgtatg tatgtttcaa    3120
ggttatttaa cagtgtacta tggttttata tcttgacttg ccttgtacat ctttcaattc    3180
tggaatatct gtgtctaagc acaatatctt cacactgtgc tgtattgctg ctgaactaaa    3240 tgcactttc cccacatatg gggcactggc ttcaaacaat tcagttcagt atcattactt     3300
ttaatctcat ctttcctttc ttggtagttg ttaatacagt tatggaaaag aggcacattg    3360
catagaagcc attggggagt tcagtggaag ttctgtaaga tgtgcatgta ctatttgatg    3420
cgttttcttt gcttcactgc ttttaatact tagcagtatt gttggtctaa gtcaatttga    3480
ttattgagga gtctcagagc aaggtgcgtt ctagatgtca tcctaaaaaa cacttcatat    3540
ataattaatc actattttgt ataattacat attgctgctt gtgtgttttt tttttttttcc   3600 atttagttgg gcgttgtgtt ttacacaaaa ccattttga attaaggcta tgatattaag     3660
atagaaattt ggactgttgt tctgcttttc ctggcactca aattcatgac tagttttgag    3720
gtcaaaccta tgttcgtaat gagagatttt ataaggatca actaagaaat ggaaggcagg    3780
tgaagatata aaaccctaga atgcttaaat gtgctgtaaa actattgtag atgtcactgg    3840
attttaccaa gtaatatcct ttcttttttt tttccccca tctgctgtgg cttttcagtt     3900
aaaattttgt ttataaaagg aatttgttta ttacagctct acctagaaaa aaaaaaaaaa    3960
aa                                                                   3962
```

<210> SEQ ID NO 2
<211> LENGTH: 3962
<212> TYPE: DNA
<213> ORGANISM: Homo sapiens

<400> SEQUENCE: 2

```
gagtgggga ggggcgggcg gggggcggcg gttgggcagc gtcgcttctt aggaggagga      60
ggaagaggag gaaggagggc gagcgaggag gatggcggag tcgggctcc tgacggaact     120 ctaatgaatc attgattgac cagcactatt ttaccagttg gaatgaatga tcagaaatgg    180
gcatagtgct tttagatcca acatgtaaca gatggatgtt actccatgct gattacttct    240
tcaagccagt acttttttga ttgtgtagga tcttttgtctc ttcatctttg aattcaatta   300
ctggaaaata aaaggagttc atgtagttttt tgtccaggct tgagtcacca tgggtagtag   360
tttaggaaaa gaaaaagact ctaaagaaaa agatcccaaa gtaccatcag ccaaggaaag    420
agaaaaggag gcaaaagcct ctggaggttt tgggaaagag agcaaagaaa aagaacctaa    480
gaccaaaggg aaagatgcca aagatggaaa gaaggactcc agtgctgccc aaccaggggt    540
ggcattttca gttgacaata cgatcaaacg gccaaaccca gcacctggga ctagaaaaaa    600
atccagcaat gcagaggtga ttaaagagct caacaaatgc cgggaagaga attcaatgcg    660
tttggactta tccaagagat ctatacacat attgccatca tcaatcaaag agttgactca    720
attaacagaa ctttatttat acagtaacaa attgcagtcc ctcccagcag aggtgggatg    780
tttagtaaat ctcatgacac tggctctaag tgaaaattca cttaccagtt tgcctgactc    840
tcttgataac ttgaagaagc tgcggatgct tgatttacgg cataataaac tgagagaaat    900
tccttcagtg gtgtataggc tggattctct caccactctt taccttcgct ttaatcgtat    960
aactactgtg gaaaaggaca tcaaaaactt gtcaaaactc agcatgctta gcattcgaga   1020
gaacaaaatt aaacaactac ctgctgaaat tggtgaatta tgtaacctca ttacgctgga   1080
tgtagctcac aatcaacttg aacaccttcc aaaggagatt ggaaactgta cacagataac   1140
caaccttgac ttgcagcaca atgaactgct agacctccca gatactatag gaaacctgtc   1200
```

```
cagtttaagt cgtcttggtc tgagatataa cagactgtca gcaatacccca gatcattagc    1260 aaaatgcagt gcacttgaag aattaaattt agagaacaat aacatttcta ctttaccaga    1320
gagtctttta tcaagtcttg tgaaactgaa tagtttgacc ttagctagaa attgcttcca    1380
gttgtatcca gtgggtggtc catctcagtt ttctaccatc tattccctca acatggaaca    1440
caatcgaatc aacaaaattc catttggaat tttctccaga gcaaaagtat taagtaagct    1500
gaatatgaag gacaatcagt taacatcact tcccttggat tttggaactt ggaccagtat    1560
ggtagaattg aatttagcca ctaatcagct cacaaagatc cctgaggatg tgtctggtct    1620
cgtttctctt gaggttctta tcttatcaaa caatcttcta aagaagcttc cccatggtct    1680 tggaacccctt aggaagttaa gagagttgga tctagaagag aacaaattgg aatccttgcc    1740
aaatgaaatt gcatatctta aggatttaca gaaattagtc ttgacaaaca accagttgac    1800
cactcttccc agaggcattg gtcaccttac taatctcaca catctgggcc ttggagagaa    1860
cctacttact caccttcctg aagaaattgg tacactggag aacctagaag aactgtattt    1920
gaatgacaac cccaacctgc atagccttcc ctttgagctg gcactctgca gcaagctttc    1980
aatcatgagt attgagaact gtccactcag tcaccttcca cctcagattg ttgctggggg    2040
gccttctttc atcattcagt tcttaaagat gcagggtcca tatcgtgcca tggtctgata    2100
taaatctgct ggtcccacac actgttcaaa aatagactgc cattaatgtt tcttatctat    2160
atctgtatct atttatgtag atattggtat atggcagatt tataaaaatt gcattatgtg    2220
tttctgctaa tagaggaatc atagccattt agaattttttt ttaaattctg tacaaaaggc    2280
ttatataagt tttctttgct gaatttgatg gatgtttttc tgttgtgtaa tctgatatgc    2340
cagtttgctt aaaacatttg ccaacacatt atgaagttat taaatttaag ggacagaggt    2400
agtatagtta gatatacttt ctcttaggaa aaataatggg caaaaatttt tgttgcaact    2460
tttcatatat atttttcccct taccaattgt tttatcctta tagtattgta ggccctgaaa    2520
gtagaatttt tctttaactt attttgagat ttgagattta aattttatgt attgtttaca    2580
gtcagagtaa atcactggat ttcttttgtt tgttttgatt tgctctgttt tattcagtca    2640
aatctagagt ttgaatcctc tgctaaagaa tttgcatcca ctggtgtaaa cagtgaaagg    2700
tatttgcttg ttgaaaaaaa aaactggcaa agtgaaaaga tacagtcaaa aatctagaat    2760
ttctttaatt ttgcttctct gacgagttgt gaagcaaaat acctgaagtg agtctttggg    2820
taggggaagg gtattgagac ctttttctagt atgaatattt tttaagtttg ggggaagaga    2880
aacttgcagt gaaaaggagt tttttcattc ctgaaagttg cagatccaca aaactaacag    2940
gataattggg caaataaatt acatataaac acacacaatc tatatatgta tatacaatgc    3000
tatatagata tgtatttatt atatcataaa ctacagtagg taactttaag gatttcttcc    3060
tatccttgta caatgacatg aatgtctttc tttgaaaact gcaatgtatg tatgtttcaa    3120
ggttatttaa cagtgtacta tggttttata tcttgacttg ccttgtacat ctttcaattc    3180
tggaatatct gtgtctaagc acaatatctt cacactgtgc tgtattgctg ctgaactaaa    3240 tgcactttttc cccacatatg gggcactggc ttcaaacaat tcagttcagt atcattactt    3300
ttaatctcat ctttccttttc ttggtagttg ttaatacagt tatggaaaag aggcacattg    3360
catagaagcc attggggagt tcagtggaag ttctgtaaga tgtgcatgta ctatttgatg    3420
cgttttcttt gcttcactgc ttttaatact tagcagtatt gttggtctaa gtcaatttga    3480
ttattgagga gtctcagagc aaggtgcgtt ctagatgtca tcctaaaaaa cacttcatat    3540
```

```
ataattaatc actattttgt ataattacat attgctgctt gtgtgttttt ttttttttcc    3600
atttagttgg gcgttgtgtt ttacacaaaa ccattttga attaaggcta tgatattaag    3660
atagaaattt ggactgttgt tctgcttttc ctggcactca aattcatgac tagttttgag    3720
gtcaaaccta tgttcgtaat gagagatttt ataaggatca actaagaaat ggaaggcagg    3780
tgaagatata aaaccctaga atgcttaaat gtgctgtaaa actattgtag atgtcactgg    3840
attttaccaa gtaatatcct ttctttttt tttccccca tctgctgtgg cttttcagtt     3900
aaaattttgt ttataaaagg aatttgttta ttacagctct acctagaaaa aaaaaaaaaa    3960
aa                                                                    3962
```

<210> SEQ ID NO 3
<211> LENGTH: 582
<212> TYPE: PRT
<213> ORGANISM: Homo sapiens

<400> SEQUENCE: 3

```
Met Ser Ser Ser Leu Gly Lys Glu Lys Asp Ser Lys Glu Lys Asp Pro
  1               5                  10                  15

Lys Val Pro Ser Ala Lys Glu Arg Glu Lys Glu Ala Lys Ala Ser Gly
             20                  25                  30

Gly Phe Gly Lys Glu Ser Lys Glu Lys Glu Pro Lys Thr Lys Gly Lys
         35                  40                  45

Asp Ala Lys Asp Gly Lys Lys Asp Ser Ser Ala Ala Gln Pro Gly Val
     50                  55                  60

Ala Phe Ser Val Asp Asn Thr Ile Lys Arg Pro Asn Pro Ala Pro Gly
 65                  70                  75                  80

Thr Arg Lys Lys Ser Ser Asn Ala Glu Val Ile Lys Glu Leu Asn Lys
                 85                  90                  95

Cys Arg Glu Glu Asn Ser Met Arg Leu Asp Leu Ser Lys Arg Ser Ile
            100                 105                 110

His Ile Leu Pro Ser Ser Ile Lys Glu Leu Thr Gln Leu Thr Glu Leu
        115                 120                 125

Tyr Leu Tyr Ser Asn Lys Leu Gln Ser Leu Pro Ala Glu Val Gly Cys
    130                 135                 140

Leu Val Asn Leu Met Thr Leu Ala Leu Ser Glu Asn Ser Leu Thr Ser
145                 150                 155                 160

Leu Pro Asp Ser Leu Asp Asn Leu Lys Lys Leu Arg Met Leu Asp Leu
                165                 170                 175

Arg His Asn Lys Leu Arg Glu Ile Pro Ser Val Val Tyr Arg Leu Asp
            180                 185                 190

Ser Leu Thr Thr Leu Tyr Leu Arg Phe Asn Arg Ile Thr Thr Val Glu
        195                 200                 205

Lys Asp Ile Lys Asn Leu Ser Lys Leu Ser Met Leu Ser Ile Arg Glu
    210                 215                 220

Asn Lys Ile Lys Gln Leu Pro Ala Glu Ile Gly Glu Leu Cys Asn Leu
225                 230                 235                 240

Ile Thr Leu Asp Val Ala His Asn Gln Leu Glu His Leu Pro Lys Glu
                245                 250                 255

Ile Gly Asn Cys Thr Gln Ile Thr Asn Leu Asp Leu Gln His Asn Glu
            260                 265                 270

Leu Leu Asp Leu Pro Asp Thr Ile Gly Asn Leu Ser Ser Leu Ser Arg
        275                 280                 285

Leu Gly Leu Arg Tyr Asn Arg Leu Ser Ala Ile Pro Arg Ser Leu Ala
```

```
                    290                 295                 300
Lys Cys Ser Ala Leu Glu Glu Leu Asn Leu Glu Asn Asn Ile Ser
305                 310                 315                 320

Thr Leu Pro Glu Ser Leu Leu Ser Ser Leu Val Lys Leu Asn Ser Leu
                    325                 330                 335

Thr Leu Ala Arg Asn Cys Phe Gln Leu Tyr Pro Val Gly Gly Pro Ser
                    340                 345                 350

Gln Phe Ser Thr Ile Tyr Ser Leu Asn Met Glu His Asn Arg Ile Asn
                    355                 360                 365

Lys Ile Pro Phe Gly Ile Phe Ser Arg Ala Lys Val Leu Ser Lys Leu
                    370                 375                 380

Asn Met Lys Asp Asn Gln Leu Thr Ser Leu Pro Leu Asp Phe Gly Thr
385                 390                 395                 400

Trp Thr Ser Met Val Glu Leu Asn Leu Ala Thr Asn Gln Leu Thr Lys
                    405                 410                 415

Ile Pro Glu Asp Val Ser Gly Leu Val Ser Leu Glu Val Leu Ile Leu
                    420                 425                 430

Ser Asn Asn Leu Leu Lys Lys Leu Pro His Gly Leu Gly Asn Leu Arg
                    435                 440                 445

Lys Leu Arg Glu Leu Asp Leu Glu Glu Asn Lys Leu Glu Ser Leu Pro
                    450                 455                 460

Asn Glu Ile Ala Tyr Leu Lys Asp Leu Gln Lys Leu Val Leu Thr Asn
465                 470                 475                 480

Asn Gln Leu Thr Thr Leu Pro Arg Gly Ile Gly His Leu Thr Asn Leu
                    485                 490                 495

Thr His Leu Gly Leu Gly Glu Asn Leu Leu Thr His Leu Pro Glu Glu
                    500                 505                 510

Ile Gly Thr Leu Glu Asn Leu Glu Glu Leu Tyr Leu Asn Asp Asn Pro
                    515                 520                 525

Asn Leu His Ser Leu Pro Phe Glu Leu Ala Leu Cys Ser Lys Leu Ser
                    530                 535                 540

Ile Met Ser Ile Glu Asn Cys Pro Leu Ser His Leu Pro Pro Gln Ile
545                 550                 555                 560

Val Ala Gly Gly Pro Ser Phe Ile Ile Gln Phe Leu Lys Met Gln Gly
                    565                 570                 575

Pro Tyr Arg Ala Met Val
                    580

<210> SEQ ID NO 4
<211> LENGTH: 420
<212> TYPE: PRT
<213> ORGANISM: Home sapiens

<400> SEQUENCE: 4

Met Gly Ser Ser Leu Gly Lys Glu Lys Asp Ser Lys Glu Lys Asp Pro
1               5                   10                  15

Lys Val Pro Ser Ala Lys Glu Arg Glu Lys Glu Ala Lys Ala Ser Gly
                    20                  25                  30

Gly Phe Gly Lys Glu Ser Lys Glu Lys Glu Pro Lys Thr Lys Gly Lys
                    35                  40                  45

Asp Ala Lys Asp Gly Lys Lys Asp Ser Ser Ala Ala Gln Pro Gly Val
                    50                  55                  60

Ala Phe Ser Val Asp Asn Thr Ile Lys Arg Pro Asn Pro Ala Pro Gly
65                  70                  75                  80
```

```
Thr Arg Lys Lys Ser Ser Asn Ala Glu Val Ile Lys Glu Leu Asn Lys
                85                  90                  95

Cys Arg Glu Glu Asn Ser Met Arg Leu Asp Leu Ser Lys Arg Ser Ile
            100                 105                 110

His Ile Leu Pro Ser Ser Ile Lys Glu Leu Thr Gln Leu Thr Glu Leu
        115                 120                 125

Tyr Leu Tyr Ser Asn Lys Leu Gln Ser Leu Pro Ala Glu Val Gly Cys
    130                 135                 140

Leu Val Asn Leu Met Thr Leu Ala Leu Ser Glu Asn Ser Leu Thr Ser
145                 150                 155                 160

Leu Pro Asp Ser Leu Asp Asn Leu Lys Lys Leu Arg Met Leu Asp Leu
                165                 170                 175

Arg His Asn Lys Leu Arg Glu Ile Pro Ser Val Val Tyr Arg Leu Asp
            180                 185                 190

Ser Leu Thr Thr Leu Tyr Leu Arg Phe Asn Arg Ile Thr Thr Val Glu
        195                 200                 205

Lys Asp Ile Lys Asn Leu Ser Lys Leu Ser Met Leu Ser Ile Arg Glu
    210                 215                 220

Asn Lys Ile Lys Gln Leu Pro Ala Glu Ile Gly Glu Leu Cys Asn Leu
225                 230                 235                 240

Ile Thr Leu Asp Val Ala His Asn Gln Leu Glu His Leu Pro Lys Glu
                245                 250                 255

Ile Gly Asn Cys Thr Gln Ile Thr Asn Leu Asp Leu Gln His Asn Glu
            260                 265                 270

Leu Leu Asp Leu Pro Asp Thr Ile Gly Asn Leu Ser Ser Leu Ser Arg
        275                 280                 285

Leu Gly Leu Arg Tyr Asn Arg Leu Ser Ala Ile Pro Arg Ser Leu Ala
    290                 295                 300

Lys Cys Ser Ala Leu Glu Glu Leu Asn Leu Glu Asn Asn Asn Ile Ser
305                 310                 315                 320

Thr Leu Pro Glu Ser Leu Leu Ser Ser Leu Val Lys Leu Asn Ser Leu
                325                 330                 335

Thr Leu Ala Arg Asn Cys Phe Gln Leu Tyr Pro Val Gly Gly Pro Ser
            340                 345                 350

Gln Phe Ser Thr Ile Tyr Ser Leu Asn Met Glu His Asn Arg Ile Asn
        355                 360                 365

Lys Ile Pro Phe Gly Ile Phe Ser Arg Ala Lys Val Leu Ser Lys Leu
    370                 375                 380

Asn Met Lys Asp Asn Gln Leu Thr Ser Leu Pro Leu Asp Phe Gly Thr
385                 390                 395                 400

Trp Thr Ser Met Val Glu Leu Asn Leu Ala Thr Asn Gln Leu Thr Lys
                405                 410                 415

Ile Pro Glu Asp
            420

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
gtgtaggatc tttgtctctt c                                             21
```

```
<210> SEQ ID NO 6
<211> LENGTH: 21
<212> TYPE: DNA
<213> ORGANISM: Artificial Sequence
<220> FEATURE:
<223> OTHER INFORMATION: PCR Primer

<400> SEQUENCE: 6
ccttctttcc atctttggca t                                              21
```